United States Patent [19]

Campbell et al.

[11] Patent Number: 5,308,752
[45] Date of Patent: May 3, 1994

[54] DIAGNOSIS OF AUTOSOMAL MUSCULAR DYSTROPHY

[75] Inventors: Kevin P. Campbell; Kiichiro Matsumura, both of Iowa City, Iowa

[73] Assignee: Univ. of Iowa Research Foundation, Oakdale, Iowa

[21] Appl. No.: 946,234

[22] Filed: Sep. 14, 1992

Related U.S. Application Data

[63] Continuation-in-part of Ser. No. 841,654, Feb. 20, 1992, Pat. No. 5,260,209, which is a continuation-in-part of Ser. No. 527,583, May 23, 1990, Pat. No. 5,187,063.

[51] Int. Cl.$^5$ ............................................. G01N 33/567
[52] U.S. Cl. .................................. 435/7.21; 435/960; 436/63; 436/518; 436/811; 530/387.9; 530/389.1
[58] Field of Search ................ 435/7.21, 960; 436/63, 436/518, 811; 530/387.9, 389.1

[56] References Cited

U.S. PATENT DOCUMENTS 4,912,202  3/1990  Campbell et al. ................ 530/388.2
5,187,063  2/1993  Campbell et al. ................. 435/7.21

FOREIGN PATENT DOCUMENTS

0331514A2  9/1989  European Pat. Off. .
WO89/06286  7/1989  PCT Int'l Appl. .

OTHER PUBLICATIONS

Matsumura et al., Abnormal expression of dystrophin-associated proteins in Fukuyama-type Congenital muscular dystriophy. The Lancet 341:521–522, 1993.
Ervasti et al., Deficiency of a glycoprotein component of the dystrophic complex in dystrophic muscle. Nature 345:315–319, 1990.
Hoffman, E. P., et al., Cell, 51: 919–928 (1987).
Knudson, C. M., et al., J. of Biol. Chem., 263(17): 8480–8484 (1988).
Hoffman, E. P., et al., N.E. J. Med., 318(21): 1363–1368 (1988).
Zubrzycka-Gaarn, E. E., et al., Nature, 333: 466–469 (1988).
Arahata, K., et al., Nature, 333: 861–863 (1988).
Bonilla, E., et al., Cell, 54: 447–452 (1988).
Cooper, B. J., et al., Nature, 334: 154–156 (1988).
Campbell, K. P., and Kahl, S. D., Nature, 338: 259–262 (1989).
Ervasti, J. M. et al., Nature, 345: 315–319 (1990).
A. O. Jorgensen et al. The Journal of Cell Biology 110:1173–1185 (1990).
Sevier et al., Clin. Chem. 271: 1797–1806 (1981).
Ben Hamida et al., J. Meurol. Sci. 107 60–64 (1992).
Ibraghimov-Beskrovnaya et al., Nature 355: 696 (1992).
Ohlendieck and Campbell, J. Cell Biol. 115 1685–1694 (1991).
Ervasti and Campbell Cell 66:1121–1131 (1991).

Primary Examiner—Esther L. Kepplinger
Assistant Examiner—Donna C. Wortman
Attorney, Agent, or Firm—Kevin M. Farrell

[57] ABSTRACT

Disclosed are methods for the diagnosis of autosomal muscular dystrophy through the analysis of muscle tissue using antibodies reactive with components of the dystrophin-glycoprotein complex. An experimental muscle tissue sample, treated if necessary to render components of the dystrophin-glycoprotein complex available for antibody binding, is contacted with an antibody which binds to a dystrophin-associated protein. The extent of antibody binding is determined, and compared to the extent of antibody binding to normal control tissue. A substantial reduction in the extent of binding to experimental tissue, as compared with normal control tissue, being diagnostic of autosomal muscular dystrophy. Among the autosomal muscular dystrophies which are detectable by the methods described herein are Fukuyama muscular dystrophy and severe childhood autosomal recessive muscular dystrophy.

7 Claims, No Drawings

5,308,752

DIAGNOSIS OF AUTOSOMAL MUSCULAR DYSTROPHY

RELATED APPLICATIONS

This application is a continuation-in-part of Ser. No. 07/841,654, filed Feb. 20, 1992, now U.S. Pat. No. 5,260,209, which is a continuation-in-part of the United States designation in International Application No. PCT/US91/03632, filed May 23, 1991, which is a continuation-in-part of U.S. application Ser. No. 527,583, filed May 23, 1990, now U.S. Pat. No. 5,187,0 the contents of which are incorporated herein by reference.

BACKGROUND OF THE INVENTION

Severe childhood autosomal recessive muscular dystrophy (SCARMD) is a disease which is prevalent in North Africa. This progressive muscular dystrophy shares several clinical features with Duchenne's muscular dystrophy (DMD) including, for example, mode of onset, rapid progression, hypertrophy of calves and extremely high serum creatine kinase levels during the initial stages of the disease (see, e.g., Ben Hamida et al., J. Neurol Sci. 107: 60–64 (1992)).

It has been demonstrated that Duchenne's muscular dystrophy is caused by a mutation or deletion which results in the absence of the dystrophin protein (Hoffman et al., Cell 51: 919–928 (1987)). Dystrophin has been shown to be associated with a large oligomeric complex of sarcolemmal glycoproteins (see, e.g., Ervasti and Campbell, Cell 66: 1121–1131 (1991)). The dystrophin-glycoprotein complex has been proposed to span the sarcolemma and provide a linkage between the subsarcolemmal cytoskeleton and the extracellular matrix. In DMD, the absence of dystrophin leads to a great reduction in all of the dystrophin-associated proteins. These observations have enabled, for example, the development of immunologically-based methods for the diagnosis of DMD.

In contrast to DMD, it has been reported that dystrophin and dystrophin-related protein (DRP), an autosomal homologue of dystrophin, are expressed normally in the skeletal muscle of individuals afflicted with SCARMD (see, e.g., Khurana et al., Neuromusc. Dis. 1: 185–194 (1991)). Thus, there is no teaching in the prior art which would enable the development of an immunologically-based method for diagnosing SCARMD, or other autosomal muscular dystrophies.

SUMMARY OF THE INVENTION

The subject invention relates to methods for the diagnosis of autosomal muscular dystrophy through the analysis of muscle tissue using antibodies reactive with components of the dystrophin-glycoprotein complex. An experimental muscle tissue sample, treated if necessary to render components of the dystrophin-glycoprotein complex available for antibody binding, is contacted with an antibody which binds to a dystrophin-associated protein. The extent of antibody binding is determined, and compared to the extent of antibody binding to normal control tissue. A substantial reduction in the extent of binding to experimental tissue, as compared with normal control tissue, has been determined to be diagnostic of autosomal muscular dystrophy.

Among the autosomal muscular dystrophies which are detectable by the methods described herein are Fukuyama muscular dystrophy and severe childhood autosomal recessive muscular dystrophy. The former is characterized by a substantial reduction in all dystrophin-associated proteins, and the latter is characterized by a substantial reduction in the 50 kDa dystrophin-associated glycoprotein.

DETAILED DESCRIPTION OF THE INVENTION

Dystrophin is a large molecular weight protein product of the defective gene responsible for Duchenne's Muscular Dystrophy. This invention is based, in part, on the discovery that dystrophin exists as a component of a large oligomeric complex in the sarcolemmal membrane of normal skeletal muscle. Proteins and glycoproteins comprise the other components of this complex which is referred to herein as the dystrophin-glycoprotein complex. Specifically, the other components comprise a 156 kDa glycoprotein, a 50 kDa glycoprotein, a 43 kDa glycoprotein, a 35 kDa glycoprotein, a 25 kDa protein and a triplet of proteins of 59 kDa molecular weight. These components are referred to as the non-dystrophin components of the dystrophin-glycoprotein complex.

Isolation of the Dystrophin-Glycoprotein Complex

The dystrophin-glycoprotein complex can be isolated from detergent solubilized skeletal muscle membranes using affinity chromatography and density gradient ultracentrifugation. Lectins are proteins or glycoproteins which bind certain sugars or oligosaccharides. This property can be used to isolate certain glycoproteins from a complex mixture and is extremely useful as a general approach to the purification of membrane proteins, many of which are glycosylated. In the present invention, the linked components of the dystrophin-glycoprotein complex can be isolated as an intact complex with lectins that bind to the glycoprotein components of the complex. The lectins are typically coupled to a solid support such as a chromatographic gel (i.e., sepharose, agarose, etc.) and a complex mixture of membrane components is passed through a chromatography column containing the gel with bound lectin. The glycoproteins of membrane components bind to the lectin while the other components of the mixture pass through the column. As described in greater detail below, a variety of lectins can be used in affinity-based methodologies to isolate the dystrophin-glycoprotein complex.

The dystrophin-glycoprotein complex can be further purified using density gradient ultracentrifugation. The eluate from the affinity column as described above is applied as a narrow band to the top of a solution in a centrifuge tube. To stabilize the sedimenting components of the eluate against convection mixing, the solution beneath the band contains an increasingly dense solution of an inert, highly soluble material such as sucrose (a density gradient). Under these conditions, the different fractions of the eluate sediment at different rates forming distinct bands that can be individually collected. The rate at which each component sediments depends on its size and shape and is normally expressed as its sedimentation coefficient or S value.

Present day ultracentrifuges rotate at speeds up to about 80,000 rpm and produce forces up to about 500,000×gravity. At these enormous forces, even relatively small macromolecules, such as tRNA molecules and simple enzymes, separate from one another on the basis of their size. Using this technique, the size of the dystrophin-glycoprotein complex was estimated to be approximately 18S by comparing its migration to that of standards of varying size.

Another form of affinity chromatography which can be used to isolate the dystrophin-glycoprotein complex is known as immunoaffinity purification. This technique utilizes the unique high specificity of polyclonal and monoclonal antibodies as well as selected lectins. Such highly specific molecules are extremely valuable tools for rapid, selective purification of antigens. In principle, the antigen is coupled (immobilized) on a column support and this is used to selectively adsorb antigen from a mixture containing many other antigens. The antigens for which the antibody has no affinity can be washed away, and the purified antigen then eluted from the bound antibody or lectin with an elution buffer. Examples of antibodies and lectin molecules which are useful for the immunopurification of the dystrophin complex components are described in detail below.

The separation and isolation of the components of the dystrophin-glycoprotein complex can be accomplished by SDS-polyacrylamide gel electrophoresis (SDS-PAGE). In this technique, proteins are reacted with the detergent sodium dodecylsulfate (SDS), to form negatively charged complexes. The amount of SDS bound by a protein, and consequently the charge on the complex, is roughly proportional to its size. Commonly, about 1.4 grams SDS is bound per 1 gram protein, although there are exceptions to this rule. The proteins are generally denatured and solubilized by their binding of SDS, and the complex forms a prolate ellipsoid or rod of a length roughly proportionate to the molecular weight of the protein. Thus, proteins of either acidic or basic isoelectric point form negatively charged complexes that can be separated on the basis of differences in charges and sizes by electrophoresis through a sieve-like matrix of polyacrylamide gel.

An alternative method for isolating the components of the dystrophin-glycoprotein complex is gel filtration high pressure liquid chromatography. This technique, in addition to taking less time than SDS gel electrophoresis, allows easier quantitation and recovery of separated proteins, and the resolution is better than that achieved by gel filtration with conventional materials.

Preparation of Antibodies Reactive with Components of the Dystrophin-Glycoprotein Complex Monoclonal and polyclonal antibodies specific for non-dystrophn components of the dystrophin-glycoprotein complex are particularly useful in the isolation and diagnostic methods of this invention. Monoclonal antibodies useful in this invention are obtained by well known hybridoma methods. An animal is immunized with a preparation containing the dystrophin-glycoprotein complex. A fused cell hybrid is then formed between antibody-producing cells from the immunized animal and an immortalizing cell such as a myeloma.

In preferred embodiments, anti-non-dystrophin component monoclonal antibodies of this invention are produced by murine hybridomas formed by fusion of: a) mouse myeloma or hybridoma which does not secrete antibody with b) murine spleen cells which secrete antibodies obtained from mice immunized against dystrophin-glycoprotein complex.

Typically, the mice are immunized with a primary injection of dystrophin-glycoprotein complex followed by a number of boosting injections of dystrophin-glycoprotein complex. During or after the immunization procedure, sera of the mice may be screened to identify those mice in which a substantial immune response to the complex has been evoked. From selected mice, the spleen cells are obtained and fusions are performed. Suitable fusion techniques are the Sendai virus technique (Kohler, G. and Milstein, C., *Nature*, 256: 495 (1975)), or the polyethylene glycol method (Kennet, R.H., "Monoclonal Antibodies, Hybridomas—A New Dimension in Biological Analysis," Eds. R.H. Kennet, T.J. McKern and K.B. Bechtol, Plenum Press, NY (1980)).

The hybridomas are then screened for production of anti-non-dystrophin component antibodies. A suitable screening technique is a solid phase radioimmunoassay. A solid phase immunoadsorbent is prepared by coupling dystrophin-glycoprotein complex or non-dystrophin components to an insoluble matrix. The immunoadsorbent is brought into contact with culture supernatants of hybridomas. After a period of incubation, the solid phase is separated from the supernatants, then contacted with a labeled antibody against murine immunoglobulin. Label associated with the immunoadsorbent indicates the presence of hybridoma products reactive with dystrophin-glycoprotein complexes or non-dystrophin components. The hybridoma products are then examined for their ability to react with natural and synthetic components of the dystrophin-glycoprotein complex.

The monoclonal anti-non-dystrophin component antibodies can be produced in large quantities by injecting anti-non-dystrophin component antibody producing hybridoma cells into the peritoneal cavity of mice and, after an appropriate time, harvesting acites fluid from the mice which yield a high titer of homogenous antibody. The monoclonal antibodies are isolated therefrom. Alternatively, the antibodies can be produced by culturing anti-non-dystrophin component antibody producing cells in vitro and isolating secreted monoclonal anti-non-dystrophin component antibodies from the cell culture medium directly.

Another method of forming antibody-producing cells is by viral or oncogenic transformation. For example, a B-lymphocyte which produced a non-dystrophin component specific antibody may be infected and transformed with a virus, such as the Epstein-Barr virus, to give an immortal antibody-producing cell (Kozbon and Roder, *Immunol. Today* 4: 72–79 (1983)). Alternatively, the B-lymphocyte may be transformed by a transforming gene or gene product.

Polyclonal antibodies can be prepared by immunizing an animal with a crude preparation of the dystrophin-glycoprotein complex or the purified non-dystrophin components of the complex. The animal is maintained under conditions whereby antibodies reactive with the components of the complex are produced. Blood is collected from the animal upon reaching a desired titer of antibodies. The serum containing the polyclonal antibodies (antisera) is separated from the other blood components. The polyclonal antibody-containing serum can optionally be further separated into fractions of particular types of antibodies (e.g., IgG or IgM) or monospecific antibodies can be purified from polyolonal antibody containing serum.

Diagnostic Methods

An observation which is fundamental to the subject invention is that there is a strong correlation between the absence or reduction in the quantity of the non-dystrophin components of the dystrophin-glycoprotein complex and affliction by muscular dystrophy. As described in the Exemplification below, monoclonal or polyclonal antibodies can be used to detect the absence or reduction of a particular non-dystrophin component of the complex. In both mouse and human samples of dystrophic tissue, muscular dystrophy can be diagnosed by detecting reduction or absence of non-dystrophin components of the complex. This analysis can be extended beyond the Duchenne-type muscular dystrophy (X-linked) to the detection of autosomal-based muscular dystrophy as demonstrated in the Examples below in connection with Fukuyama congenital muscular dystrophy and severe childhood autosomal recessive muscular dystrophy (SCARMD).

In one embodiment of the diagnostic method of the invention, a muscle biopsy sample is treated in a procedure which renders the non-dystrophin components available for complexing with antibodies directed against said components. Muscle samples are obtained from patients by surgical biopsy. The site of biopsy could be any skeletal muscle suspected of being dystrophic. Muscle groups about the shoulder and pelvic girdles, however, are the most affected, and are likely to be the most common site of biopsy. The amount of muscle obtained should be enough to extract the components of the dystrophin-glycoprotein complex from muscle membranes and detect their presence by the diagnostic methods described within this application. Alternative methods of extraction can be used.

For biopsy samples greater than 500 mg, the muscle tissue can be homogenized by mechanical disruption using apparatus such as a hand operated or motor driven glass homogenizer, a Waring blade blender homogenizer, or an ultrasonic probe. Homogenization can occur in a buffer comprising 20 mM sodium pyrophosphate, 20 mM sodium phosphate monohydrate, 1 mM magnesium chloride, 0.303 M sucrose, 0.5 mM EDTA, pH 7.1, with various protease inhibitors such as aprotinin (0.5 $\mu$g/ml), benzamidine (100 $\mu$g/ml), iodoacetamide (185 $\mu$g/ml), leupeptin (0.5 $\mu$g/ml), pepstatin A (0.5 $\mu$g/ml) and PMSF (40 $\mu$g/ml). Heavy microsomes can be prepared from homogenized skeletal muscle by the method of Mitchel, et al. (*J. Cell. Biol.*, 95: 1008–1016 (1983)). The microsomes are then washed with a physiological salt solution and solubilized in saline containing detergent and protease inhibitors. Following solubilization of the microsomes, the sample is treated with SDS. In the present case, SDS acts to dissociate the linked components of the dystrophin-glycoprotein complex, thereby allowing their separation.

For muscle biopsy samples less than 500 mg, an alternative extraction procedure can be used. Samples are frozen in liquid nitrogen and crushed using a mortar and pestle and prepared for electrophoresis by treatment with SDS as described by Hoffman et al. (*N. Eng. J. Med.* 318: 1363–1368 (1988)), hereby incorporated by reference.

The components of the SDS treated sample are then separated electrophoretically. Following electrophoretic separation, the components of the dystrophin-glycoprotein complex are transferred from the gel matrix to a solid support. The components are transferred out of the gel and onto a filter or membrane, forming an exact replica of the original protein separation, but leaving the transferred proteins accessible for further study.

The detection of transferred proteins can be accomplished by the use of general protein dyes such as Amido black or Coomassie brilliant blue. Alternatively, antibodies which are specific for the known non-dystrophin components of the dystrophin-glycoprotein complex can be labeled with a detectable reporter group and used to bind to the various components. An example of this method is the well known Western blot method. In yet another alternative detection method, unlabeled antibodies specific for a component of the dystrophin-glycoprotein complex are incubated with a muscle tissue sample under conditions appropriate for binding. The specific binding of these antibodies to the muscle tissue sample is detected through the use of labeled secondary antibodies by conventional techniques.

Alternatively, tissue specimens (e.g., human biopsy samples) can be tested for the presence of the components of the dystrophin-glycoprotein complex by using monoclonal or polyclonal antibodies in an immunohistochemical technique, such as the immunoperoxidase staining procedure. In addition, immunofluorescent techniques can be used to examine human tissue specimens. In a typical protocol, slides containing cryostat sections of frozen, unfixed tissue biopsy samples are air-dried and then incubated with the anti-non-dystrophin component antibody preparation in a humidified chamber at room temperature. The slides are layered with a preparation of fluorescently labeled antibody directed against the monoclonal antibody. As mentioned above, labeled secondary antibodies are also useful for detection. The staining pattern and intensities within the sample are determined by fluorescent light microscopy.

The antibodies of the present invention can also be used in an enzyme-linked immunoadsorbant assay (ELISA) for determining the absence or presence of non-dystrophin components of the dystrophin-glycoprotein complex. Antibodies against non-dystrophin components to be measured are adsorbed to a solid support, in most cases a polystyrene microtiter plate. After coating the support with antibody and washing, a solubilized sample is added. If a non-dystrophin component is present for which the antibodies are specific, they will bind to the adsorbed antibodies. Next, a conjugate that will also bind to the non-dystrophin component is added. Conjugates are secondary antibody molecules to which an enzyme is covalently bound. After addition of a chromogenic substrate for the enzyme, the intensity of the colored reaction products generated will be proportional to the amount of conjugated enzyme and thus indirectly to the amount of bound non-dystrophin component. Since the intensity of the developed color is proportional to the amount of non-dystrophin component present, determination of the intensity of the color produced by a standard series of non-dystrophin component concentrations will allow the calculation of the amount of non-dystrophin component in an unknown sample. Many variations of this assay exist as described in Voller, A., Bidwell, D.E. and Bartlett, A., The Enzyme Linked Immunoadsorbent Assay (ELISA): A guide with abstracts of microplate applications, Dynatech Laboratories, Alexandria, Va. (1979) and are hereby incorporated by reference.

In another embodiment of the diagnostic method, antibodies specifically reactive with an extracellular component of the dystrophin-glycoprotein complex (e.g., the 156 kDa component) are labeled with a detectable reporter group and administered (e.g., intravenously) to an individual to be tested for muscular dystrophy using conventional immunodiagnostic methods. The extracellular components of the dystrophin-glycoprotein complex are exposed on the surface of an intact cell and therefore, are reactive with labeled circulating antibodies which have the ability to pass through capillary membranes to reach the muscle tissue surface. Thus, the disruption of the cell is not necessary for diagnosis.

Isolation of Nucleic Acids Encoding Dystrophin-Associated Proteins and Uses for Same Antibodies reactive with dystrophin-associated proteins can be used to isolate and purify nucleic acid which encodes the proteins. This can be accomplished in a variety of ways. For example, monospecific polyclonal antibodies, or monoclonal antibodies, can be used in affinity purification methods to isolate highly purified preparations of individual dystrophin-associated glycoproteins (DAGs). Using standard biochemical techniques (e.g., Edman degradation), the amino acid sequence of a portion of the protein can be determined. Using this protein sequence information, degenerative nucleic acid probes can be designed and synthesized. Such probes can be used to screen nucleic acid libraries (e.g., cDNA libraries from tissues known to express the dystrophin-associated proteins). DNA sequences identified by such a screening method can be used to isolate overlapping clones. This process leads ultimately to the reconstruction of the entire coding region.

Alternatively, monoclonal or polyclonal antibodies can be used to screen an expression library, such as a genomic DNA library prepared in the vector λgt11. The λgt11 system enables the expression of DNA fragments from a DNA library of interest (e.g., a human genomic DNA library) as a betagalactosidase fusion protein. Recombinant phage are plated on a lawn of bacteria and the recombinants are screened immunologically using conventional techniques.

Once isolated, the DNA encoding components of the dystrophin-associated proteins can be used in a variety of ways. For example, the DNA can be inserted in an expression vector. Such vectors contain all necessary regulatory signals to promote the expression of a DNA segment of interest. Expression vectors are typically either prokaryote specific, or eukaryote specific. However, vectors have been developed which can promote the expression of a DNA sequence of interest in either a prokaryotic or eukaryotic system. Such vectors are known as shuttle vectors.

Prokaryotic expression vectors are useful for the preparation of large quantities (up to milligram quantities) of the protein encoded by a DNA sequence of interest. This protein, or immunogenic peptide portions of same, can be used for example, as a source of highly pure immunogen for the generation of antibodies specific to components of the complex. Immunogenic peptides can also be produced synthetically from the known DNA sequence. Alternatively, as discussed in detail below, some proteins may be useful for therapeutic applications.

As has been discussed previously, several of the dystrophin-associated proteins are extensively glycosylated. Because prokaryotic systems do not possess the cellular machinery necessary to reproduce this glycosylation, it may be desirable to produce the proteins in a eukaryotic system using a eukaryotic expression system.

While Duchenne and Becker muscular dystrophy are characterized by the absence, or reduction in the abundance of, dystrophin (as well as the dystrophin-associated proteins) in afflicted individuals, this is not true with all forms of muscular dystrophy. It has been observed, for example, that in patients suffering from Fukuyama congenital muscular dystrophy (FCMD), all of the dystrophin-associated glycoproteins are substantially diminished whereas the abundance of dystrophin is only mildly reduced when compared to control samples.

In studies of muscle tissue from patients afflicted with severe childhood autosomal recessive muscular dystrophy (SCARMD), it was determined that the 50 kDa dystrophin-associated protein was substantially reduced whereas levels of dystrophin and other dystrophin-associated proteins were not substantially reduced. More specifically, dystrophin and the 156 kDa, 59 kDa and 43 kDa dystrophin-associated proteins were determined to be present at normal or near normal levels. The 35 kDa dystrophin-associated protein was determined to be present at a somewhat reduced level, although not reduced to the degree observed in DMD tissue.

In addition to the two examples discussed above, it is highly likely that other autosomal mutation-based muscular dystrophies result from deleterious mutations or deletions in the genes encoding one or more of the dystrophin-associated proteins. Thus, one use for a DNA expression vector encoding a dystrophin-associated protein would be to complement such a mutation.

The DNA expression vector can be introduced into the individual in a variety of ways. For example, myoblast cells can be isolated from the afflicted individual by biopsy, transformed with the expression construct in vitro and reintroduced to the afflicted individual by intramuscular injection. Alternatively, the DNA expression construct can be administered directly to the afflicted individual, for example, by intramuscular injection.

In addition to the use of expression vectors to mediate gene therapy, the administration of dystrophin-associated protein, or portions thereof, to an afflicted individual may also offer a viable therapeutic alternative. Because of the difficulties associated with introducing a protein into a cell across the cell membrane, this therapeutic approach would be most useful for muscular dystrophies characterized by the absence or reduction in abundance of an extracellular protein. The 156 kDa dystrophin-associated protein is such a protein.

In addition, the 156 kDa dystrophin-associated protein is characterized by other properties which suggest that this type of therapy would be effective. For example, as reported in the Exemplification section which follows, the 156 kDa protein binds laminin which is one of the major components of the extracellular matrix. In fact, it appears to be a high affinity laminin binding protein. Although the mechanism underlying the fact that dystrophin deficiency causes the muscle cell necrosis characteristic of muscular dystrophy is unknown, experiments suggest that dystrophin functions to link the subsarcolemmal membrane cytoskeleton through a transmembrane complex to an extracellular glycoprotein which binds laminin. Although the exact function of the 156 kDa protein is not known, muscle cells do interact with the extracellular matrix via specific cell surface receptors and thus it is likely that the 156 kDa protein is involved in the interactions between sarcolemma and extracellular matrix.

In a therapeutic method, the 156 kDa protein, or a laminin binding domain thereof, would be administered (preferably intravenously) to an afflicted individual. At the surface of the muscles tissue, the 156 kDa protein, or the laminin binding portion thereof, is expected to interact with the sarcolemma and extracellular matrix thereby stabilizing the tissue. The progress of therapy can be monitored, for example, by a combination of muscle strength measurement and muscle biopsy analysis.

The DNA sequence information can also be used in diagnostic applications. As discussed above, many of the autosomal mutation-based muscular dystrophies are likely to result from mutations in the DNA encoding a dystrophin-associated protein. Thus, one method for diagnosing autosomal muscular dystrophy involves identifying mutations in the DNA sequence encoding a dystrophin-associated protein which correlates with the disease phenotype. This can be done, for example, using immunohistochemical techniques as described in the Examples which follow. DNA encoding a dystrophin-associated protein can be isolated from an individual whose affliction has been demonstrated in such a manner. The DNA sequence of the gene from an afflicted individual can be compared with the DNA sequence of the gene from a non-afflicted individual. Using this technique, particular mutations are identified which correlate with the disease phenotype. Using this information, synthetic oligonucleotide probes can be synthesized which facilitate the rapid detection of such mutations in a DNA sample from an individual to be tested for autosomal muscular dystrophy.

For example, if the mutation which correlates with the disease phenotype is found to be a point mutation in the gene encoding the 156 kDa dystrophin-associated protein, a synthetic peptide of about 10-15 base pairs in length can be synthesized. The sequence of the synthetic peptide should have a sequence which is perfectly complementary to the appropriate region of either the normal gene or the mutant gene. Using conventional hybridization techniques it is possible to rapidly identify the presence of either the normal sequence or the mutant sequence in a sample of DNA from an individual to be tested.

The invention is now further and specifically illustrated by the following examples.

EXEMPLIFICATION

EXAMPLE 1

Isolation and Characterization of Dystrophin-Glycoprotein Complex

Isolation of complex by density centrifugation

Heavy microsomes were prepared from rabbit skeletal muscle by the method described in Mitchell, et al. (*J. Cell. Biol.* 95: 1008-1016 (1983)). The microsomes were washed twice with 0.6 M KCl in 50 mM tris-HCl, pH 7.4, 0.165 M sucrose, 0.1 mM PMSF and 0.75 mM benzamidine to remove contractile proteins. One gram of KCl-washed membranes were solubilized in 1.0% digitonin, 0.5 M NaCl, and protease inhibitors as previously described in Campbell, K.P. and Kahl, S.D., *Nature*, 338: 259-262 (1989). After removal of the ryanodine receptor by immunoaffinity chromatography as described in Imagawa et al. (*J. of Biol. Chem.* 262: 16636-16643 (1987)), the digitonin-solubilized membranes were circulated overnight in a 40 ml WGA-sepharose column, washed extensively, then eluted with three column volumes of 0.3 M N-acetyl-glucosamine.

Eluted fractions containing dystrophin were applied to a 3 ml DEAE cellulose column and sequentially eluted with the following NaCl concentrations in buffer A (0.1% digitonin, 50 mM tris-HCl, pH 7.4, 0.75 mM benzemidine, 0.1 mM PMSF): 0 mM, 25 mM, 50 mM, 75 mM, 100 mM, 110 mM and 175 mM. Sucrose gradients (12.5 ml linear 5% to 20% sucrose) containing 0.5 M NaCl and 0.01% $NaN_3$ in buffer A were prepared using a Beckman density gradient former. Dystrophin-glycoprotein complex, which eluted in fraction two (3 ml) from the DEAE-column 175 mM NaCl wash was concentrated to 0.5 ml in a centricon-100 (Amicon), layered on a sucrose gradient, and overlaid with 0.5 ml of buffer A containing 175 mM NaCl and 0.01% $NaN_3$. Gradients were centrifuged at 4° C. in a Beckman VTi 65.1 vertical rotor for 90 minutes at 200,000XG. Fractions (0.6 ml) were collected from the top of the gradients using an ISCO Model 640 density gradient fractionator.

Affinity characterization of dystrophin-glycoprotein complex

Gradient fractions were separated by SDS-PAGE (3% to 12% gradient gel) and stained with Coomassie Blue (300 ul of fractions concentrated to 50 ul with a centricon-100) or transferred to nitrocellulose and stained with various antibodies. Gel lanes were scanned with a Hoefer GS300 scanning densitometer and analyzed using GS-360 data analysis software.

Polyclonal antisera against a chemically synthesized decapeptide representing the C-terminal of dystrophin was raised in New Zealand white rabbits as previously described in Strynadka, N.C.J., et al. *J. of Virol.*, 62: 3474-3483 (1988). Hybridomas were obtained from female balb/C mice which were immunized with rabbit skeletal muscle membranes and boosted with WGA eluate as described in Jorgensen, A.O., et al., *Cell Motility and Cytoskeleton*, 9: 164-174 (1988).

It was evident from the Coomassie Blue-stained gel of sequential gradient fractions that the dystrophin-glycoprotein complex was clearly separated from the voltage-sensitive sodium channel and the dihydropyridine receptor. The size of the dystrophin-glycoprotein complex was estimated to be approximately 18 S by comparing its migration to that of the standards B-galactosidase (15.9 S), thyroglobulin (19.2 S) and the dihydropyridine receptor (20 S). Densitometric scanning of the peak dystrophin-glycoprotein containing gradient fractions revealed several proteins which copurified with dystrophin: a broad, diffusely staining component with an apparent $M_r$ of 156 kDa, 88 kDa protein, a triplet of proteins centered at 59 kDa, 50 kDa protein, a protein doublet at 43 kDa, 35 kDa protein and a 25 kDa protein.

In order to identify the glycoprotein constituents of the dystrophin-glycoprotein complex, sucrose gradient fractions were electrophoretically separated, transferred to nitrocellulose, and stained with peroxidase-conjugated WGA. Four WGA-binding proteins with apparent $M_r$ of 156 k, 50 k, 43 k and 35 k were found to strictly copurify with dystrophin. All four of the WGA-binding proteins were also stained with peroxidase-conjugated concanavalin A. In addition, the lower $M_r$ component of the 43 kDa protein doublet, apparent with Coomassie Blue staining was also stained with concanavalin A. The dystrophin-glycoprotein complex was further characterized with antibodies raised against various components of the complex. Antisera from a rabbit which was immunized with a chemically synthesized decapeptide representing the predicted C-terminal amino acid sequence of human dystrophin was found to stain a single $M_r$ protein. This protein comigrated with the predominant isoform of dystrophin stained by sheep polyclonal anti-dystrophin antibodies.

A library of monoclonal antibodies against muscle proteins eluted from WGA-sepharose was also screened for reactivity against components of the dystrophin-glycoprotein complex. Of six hybridomas which showed immunofluorescence staining only on the sarcolemma monoclonal antibodies XIXC2 and VIA4$_2$ were found to stain dystrophin on immunoblots. Both dystrophin monoclonal antibodies are IgM subtypes, and recognized both native and denatured dystrophin. Monoclonal antibody XIXC2 also recognized the minor lower $M_r$ isoform of dystrophin which appears to copurify with the more abundant isoform.

Two of the other sarcolemma-specific monoclonal antibodies were specific for components of the dystrophin-glycoprotein complex. The 50 kDa glycoprotein stained with monoclonal antibody IVD3$_1$. Monoclonal IVD3$_1$ recognized only the nonreduced form of the 50 kDa glycoprotein and it is not highly crossreactive. Monoclonal antibody VIA4$_1$ stained the 156 kDa glycoprotein which copurified with dystrophin. Monoclonal antibody VIA4$_1$ recognized the denatured form of the 156 kDa glycoprotein and is highly crossreactive.

Immunolocalization of components of the dystrophin-glycoprotein complex in rabbit muscle The indirect immunofluorescence labeling of fixed 8 μm transverse cryostat sections from rabbit gastrocnemius was carried out as described in Jorgensen, A.O., et al., supra. Sections were preincubated for 20 minutes with 5% normal goat antiserum in phosphate buffered saline, followed by a two hour incubation at 37° C. with the primary antibody (hybridoma supernatants or 1:1000 diluted antiserum). After washing in PBS, the sections were further incubated for 30 minutes at 37° C. in PBS with a 1:50 dilution of FITC-labeled goat F(ab')$_2$ anti-mouse IgG or anti-rabbit IgG and subsequently examined in a Leitz fluorescence microscope. Staining of cryostat sections was not observed with non-immune serum, nor was there any nonspecific binding to the tissue by fluorescein-labeled secondary antibody.

The antisera to the C-terminal amino acid sequence of human dystrophin showed immunofluorescence staining only on the cell periphery which indicates a restricted localization of dystrophin to the sarcolemma of rabbit skeletal muscle. This observation was confirmed by staining rabbit skeletal muscle with monoclonal antibody XIXC2 against dystrophin and, again, localization was observed in the sarcolemma of the rabbit skeletal muscle. The 50 kDa glycoprotein, stained with monoclonal IVD3$_1$, has been localized exclusively to the sarcolemmal membrane of rabbit skeletal muscle. Monoclonal antibody VIA4$_1$ exhibited weak, but specific, immunofluorescent staining of the sarcolemmal membrane consistent with its low affinity for the native 156 kDa glycoprotein. In agreement with immunofluorescence results, a rabbit membrane preparation greatly enriched in sarcolemmal proteins also exhibits a substantial enrichment in dystrophin, the 156 kDa and 50 kDa glycoproteins. Immunofluorescence staining for dystrophin, 50 kDa glycoprotein or the 156 kDa glycoprotein was equally distributed in fast and slow muscle fibers.

Immunoadsorption of the dystrophin-glycoprotein complex

Immunoaffinity beads prepared as described in Campbell, K.P., et al. *J. of Biol. Chem.*, 262: 6460–6463 (1987), were equilibrated with buffer A containing 0.5 M NaCl and then incubated overnight (12 hours) with 0.75 ml of fraction 2 from the 1.75 mM NaCl wash of the DEAE-cellulose column as described above. After pelleting, the supernatants were decanted (voids) and the affinity beads were washed with 5×0.7 ml aliquots of buffer A containing 0.5 M NaCl. The void from each affinity column and the five washes were pooled and concentrated to 375 ul in a centricon 100 (Amicon). In addition, 0.75 ml of fraction 2 was diluted to 4.2 ml with buffer A, concentrated to 375 ul and used as control. Column voids were analyzed by SDS-PAGE and immunoblotted as described above.

The voids from the XIXC2 (anti-dystrophin) and the IVD3$_1$ (anti-50 kDA glycoprotein) immunoaffinity beads contained no dystrophin, 59 kDa triplet, 50 kDa glycoprotein, 43 kDa doublet or 35 kDa proteins as detected by Coomassie Blue staining. It was apparent that both the XIXC2 (anti-dystrophin) and IVD3$_1$ (anti-50 kDA glycoprotein) immunoaffinity beads quantitatively removed dystrophin from the starting material. Analysis of the voids for the 156 kDa glycoprotein and the 50 kDa glycoprotein revealed that both the XIXC2 and the IVD3$_1$ immunoaffinity beads selectively adsorbed all but a trace of each of these glycoproteins from the voids while the voltage-sensitive sodium channel, and the alpha1 and alpha$_2$ subunits of the dihydropyridine receptor remained in the voids. As detected by peroxidase-conjugated WGA, the 43 kDa and 35 kDa glycoproteins were also adsorbed from the voids. Immunoblots of immunoaffinity beads separated on gels indicated that dystrophin, the 156 kDa and 50 kDa glycoproteins were retained by the beads and not selectively proteolyzed. Initial experiments with monoclonal VIA4$_1$ (anti-156 kDa glycoprotein) have indicated that it has too low an affinity for the native 156 kDa glycoprotein to be successful in this type of an experiment.

EXAMPLE 2

Reduction or Absence of 156 kDa Glycoprotein in Dystrophic Mammals

Immunoblot analysis of control and dystrophic mouse muscle membranes

Membranes from control and dystrophic mice (mdx) were prepared in 10% sucrose, 76.8 mM aprotinin, 0.83 mM benzamidine, 1 mM iodoacetamide, 1.1 uM leupeptin, 0.7 uM pepstatin A, 0.23 mM PMSF, 20 mM tris-maleate, pH 7.0, by centrifuging muscle homogenates for 15 minutes for 14,000 XG and subsequently pelleting the supernatant for 30 minutes at 125,000 xg followed by KCl washing as described above. Control and dystrophic mouse muscle membranes were analyzed by SDS-PAGE and immunoblotting as described above. The amount of 156 kDa glycoprotein in each preparation was estimated densitometrically from autoradiographs of identical blots incubated with $^{125}$I-labeled sheep antimouse secondary antibody.

Staining with polyclonal antisera against the C-terminal decapeptide of dystrophin revealed that dystrophin was completely absent from dystrophic mouse membranes. In addition, comparison of normal and dystrophic mouse with immunostaining by monoclonal antibody VIA4$_1$ against the 156 kDa glycoprotein revealed that the 156 kDa glycoprotein was absent or greatly reduced in dystrophic mouse membranes. Staining of identical transfers with sheep polyclonal antisera against either the ryanodine receptor, or the dihydropyridine receptor, did not differ between control and dystrophic mouse muscle membranes. Monoclonal antibody IVD3$_1$ against the 50 kDa glycoprotein did not crossreact with normal mouse membranes and, thus, could not be evaluated. The absence of the 156 kDa glycoprotein was also confirmed using SDS muscle extracts instead of isolated membranes from control and dystrophic mice. Estimation of the 156 kDa glycoprotein remaining in the dystrophic muscle membranes using $^{125}$I-labeled secondary antibodies and total membrane preparations from four different control and four different dystrophic mice revealed an average reduction of 85% in dystrophic muscle.

Immunoblot analysis of normal and dystrophic human muscle biopsies

Frozen muscle biopsy samples (50 mg) were crushed in liquid nitrogen using a mortar and a pestle and then prepared for electrophoresis as described by Hoffman, et al., *N. Eng. J. of Med.*, 318: 1363–1368 (1988). The pulverized muscle samples were transferred to ten volumes of SDS-PAGE sample buffer (10% SDS, 2 M sucrose, 4% 2-mercaptoethanol, 0.002% bromophenyl blue, 260 mM tris-HCl, pH 6.8), vortexed, and precipitated material allowed to settle. Aliquots (50 ul) of the SDS-extracted muscle samples were analyzed by SDS-PAGE and immunoblotting and the amount of 156 kDa glycoprotein was estimated.

The dystrophic samples exhibited no staining with antibodies against dystrophin by indirect immunofluorescence microscopy and immunoblotting. In contrast to the normal muscle extract, the 3 DMD samples showed greatly reduced staining for the 156 kDa glycoprotein. On the other hand, identical immunoblots stained with monoclonal antibodies against the Ca$^{2+}$-dependent ATPase revealed no difference in the staining intensity between normal and dystrophic muscle samples. Again, the amount of 156 kDa glycoprotein was estimated to be reduced by approximately 90% in DMD samples.

EXAMPLE 3

Characterization of Dystrophin-Glycoprotein Complex with Guinea Pig Antisera

Polyclonal antisera reactive with dystrophin-glycoprotein complex

Polyclonal antisera specific for various components of the dystrophin-glycoprotein complex were prepared by two methods. In the first method, (see Sharp, A.H. and Campbell, K.P., *J. Biol. Chem.* 266:9161–9165 (1989)), individual components of the dystrophin-glycoprotein complex (−500 μg) were separated by SDS-PAGE in the presence of 1% 2-mercaptoethanol. The gels were stained for 10 min with Coomassie Blue in 10% acetic acid, 25% isopropanol and destained in distilled water. Individual bands were cut from the gel and frozen in 1 ml of PBS until being used for immunization of guinea pigs. Alternatively, 50 μg of dystrophin-glycoprotein complex in buffer A (0.1% digitonin, 50 mM Tris-HCl, pH 7.4, 0.75 mM benzamidine, 0.1 mM PMSF) was used as immunogen. Animals were boosted on day 14 with 5 μg of the appropriate antigen and monthly thereafter. Antisera were collected weekly after sufficient titers had been achieved. Antisera specific for each component of the dystrophin-glycoprotein complex were affinity-purified using Immobilon-P transfers of individual proteins separated by SDS-PAGE.

Antisera from guinea pigs immunized with purified dystrophin-glycoprotein complex as described by Ervasti et al. (*J. Biol. Chem.* 266:9161–9165 (1991)), showed immunoreactivity to all components of the complex with the exception of the 50 kDa dystrophin-associated glycoprotein. Immobilon-P transfer strips containing individual components of the dystrophin-glycoprotein complex separated by SDS-polyacrylamide gel electrophoresis were used to affinity purify antibodies specific of the 156 kDa, 59 kDa, 43 kDa and 35 kDa dystrophin-associated proteins. Antibodies to the 50 kDa dystrophin-associated glycoprotein were affinity-purified from antisera obtained by immunizing a guinea pig with SDS polyacrylamide gel slices containing the reduced 50 kDa dystrophin-associated glycoprotein. Immunoblot staining of skeletal muscle microsomes, sarcolemma and purified dystrophin-glycoprotein complex demonstrated that each of the affinity-purified antibodies recognized only proteins of the same molecular weight to which they were raised and affinity purified against. This data suggests that the 156 kDa, 59 kDa, 50 kDa, 43 kDa and 35 kDa dystrophin-associated proteins are not proteolytic fragments of larger proteins or dystrophin.

Stoichiometric relationship between complex components

Densitometric analysis of Coomassie Blue-stained SDS-polyacrylamide gels containing the electrophoretically separated components of six different preparations of dystrophin-glycoprotein complex demonstrated that the 59 kDa, 50 kDa, 43 kDa, 35 kDa and 25 kDa dystrophin-associated proteins exhibited average stoichiometric ratios of 1.6±0.22, 0.82±0.11, 0.95±0.14, 1.8±0.19 and 0.36±0.12 relative to dystrophin. However, the stoichiometry of the 156 kDa dystrophin-associated glycoprotein relative to dystrophin has not been determined because it stains poorly with Coomassie Blue. Therefore, the antibody staining intensity was quantitated from autoradiograms of the immunoblots after incubation with [$^{125}$I]-Protein A and was compared to the Coomassie Blue staining intensity of dystrophin in sarcolemma and purified dystrophin-glycoprotein complex. These comparisons indicated that all components of the dystrophin-glycoprotein complex quantitatively coenrich and that the 156 kDa dystrophin-associated glycoprotein is stoichiometric with dystrophin.

Immunolocalization of dystrophin-associated proteins

The cellular localization of the dystrophin-associated proteins was determined by indirect immunofluorescence labeling of transverse cryostat sections of rabbit skeletal muscle. The affinity-purified polyclonal antibodies specific for the 156 kDa, 59 kDa, 50 kDa, 43 kDa and 35 kDa dystrophin-associated proteins exhibited immunofluorescent staining of the sarcolemmal membrane, demonstrating the unique association of these proteins with the muscle fibre plasma membrane or the intracellular cytoskeleton subjacent to the surface membrane. All five polyclonal antibodies against dystrophin-associated proteins illustrated an equal distribution between fast and slow fibers and showed enriched staining at the neuromuscular junction.

EXAMPLE 4

Characterization of Integral Membrane Components

Alkaline extraction of the dystrophin-glycoprotein complex

Consistent with predictions that it is a cytoskeletal protein, dystrophin can be extracted from skeletal muscle membranes and membranes isolated from the electric organ of Torpedo californica in the absence of detergents by simple alkaline treatment. To evaluate which components of the dystrophin-glycoprotein complex are integral membrane proteins, alkaline-treated rabbit skeletal muscle membranes were pelleted (100,000×g) and the soluble supernatant and insoluble membrane pellet analyzed by SDS-polyacrylamide gel electrophoresis and immunoblotting. The supernatant of alkaline-treated membranes contained greater than 90% of all dystrophin while the remaining pellet-associated dystrophin could by extracted with a second alkaline treatment. The 59 kDa dystrophin-associated protein was also extracted by alkaline treatment. On the other hand, dystrophin and the 59 kDa dystrophin-associated protein remained associated with the pellet in membranes diluted in identical buffers which were not titrated to pH 11. The 156 kDa, 50 kDa, 43 kDa, and 35 kDa glycoproteins were retained in the membrane pellet after alkaline treatment. The supernatants obtained from skeletal muscle membranes titrated to pH 11, and pelleted at 100,000×g were also enriched in non- or peripheral membrane proteins such as calsequestrin, the 53- and 160 kDa glycoproteins of the sarcoplasmic reticulum and actin, while the sarcoplasmic reticulum ryanodine receptor, an integral membrane protein, was retained in the pellet. That dystrophin and the 59 kDa dystrophin-associated protein can be extracted from skeletal muscle membranes by alkaline treatment in the absence of detergents demonstrates that these proteins are not integral membrane proteins and suggests both are elements of the cytoskeleton. These data further suggest that the 156 kDa, 50 kDa, 43 kDa and 35 kDa dystrophin-associated glycoproteins are integral membrane proteins.

Incorporation of [$^{125}$I] TID into purified dystrophin-glycoprotein complex

To further assess the hydrophobic nature of the components of the dystrophin-glycoprotein complex, the hydrophobic probe [$^{125}$I] TID was photoincorporated into purified dystrophin-glycoprotein complex. Hydrophobic segments (presumably transmembrane domains) of proteins can be specifically labeled with [$^{125}$I] TID. Dystrophin and the 59 kDa dystrophin-associated protein were not labeled with [$^{125}$I] TID while the 50 kDa, 43 kDa and 35 kDa dystrophin-associated glycoproteins demonstrated roughly equal incorporation of the probe. The large amount of [$^{125}$I] TID incorporation into the 25 kDa dystrophin-associated protein indicates that it is the most hydrophobic component of the complex and may explain why we have been unsuccessful in raising antibodies to it. It is not clear why the 156 kDa dystrophin-associated glycoprotein was not labeled with [$^{125}$I] TID but one explanation may be the occlusion of its transmembrane domain(s) by the other hydrophobic components of the complex.

Effect of alkaline treatment on immunoprecipitation of the dystrophin-glycoprotein complex It has been demonstrated that the components of the purified dystrophin-glycoprotein complex no longer co-sediment on sucrose density gradients after alkaline dissociation. While dystrophin, the 156 kDa and 59 kDa dystrophin-associated proteins exhibited distinct sedimentation peaks after alkaline dissociation, the 50 kDa, 43 kDa and 35 kDa dystrophin-associated glycoproteins appeared to cosediment as a complex. To determine whether the 50 kDa, 43 kDa and 35 kDa dystrophin-associated glycoproteins remains complexed after immunoprecipitation by mAb XIXC2 (dystrophin)-Sepharose or mAb IVD3$_1$ (50 kDa glycoprotein)-Sepharose was analyzed by SDS-polyacrylamide gel electrophoresis and immunoblotting. Both the dystrophin-and 50 kDa dystrophin-associated glycoprotein-antibody matrices were effective in immunoprecipitating greater than 99% of dystrophin and 96% of the 59 kDa, 50 kDa, 43 kDa and 35 kDa dystrophin-associated proteins form untreated dystrophin-glycoprotein complex. Dystrophin- and 50 kDa dystrophin-associated glycoprotein- antibody matrices immunoprecipitated 63% and 85% of the 156 kDa dystrophin-associated glycoprotein. The dystrophin-antibody matrix immunoprecipitated greater than 99% of the dystrophin from the alkaline-treated dystrophin-associated proteins and only 51% of the 59 kDa dystrophin-associated protein indicating that the interaction between dystrophin and the complex was disrupted by alkaline treatment. The 50 kDa dystrophin-associated glycoprotein-antibody matrix immunoprecipitated less than 25%, 32% and 43% of dystrophin-associated proteins from the alkaline-treated complex. However, 96% of the 50 kDa, 43 kDa and 35 kDa dystrophin-associated glycoproteins were immunoprecipitated from the alkaline-treated complex using the 50 kDa dystrophin-associated glycoprotein antibody matrix. Thus, these data demonstrate that the 50 kDa, 43 kDa and 35 kDa dystrophin-associated proteins alone form a tightly-associated complex. Since the 50 kDa dystrophin-associated glycoprotein-antibody matrix immunoprecipitates more of the 156 kDa dystrophin-associated glycoprotein that the dystrophin-antibody matrix, these data further suggest that the 156 kDa dystrophin-associated glycoprotein is directly linked to the 50 kDa, 43 kDa and 35 kDa glycoprotein complex rather than to dystrophin.

EXAMPLE 5

Dystrophin-Associated Protein Expression in Normal and Dystrophic Murine Skeletal Muscle Isolation of skeletal and cardiac muscle membranes Skeletal and cardiac muscle membranes were prepared from age-matched normal control mice and mdx mice. During the isolation procedure, membrane preparations from different mice were not combined but kept separate for comparative purposes. Hind leg and back muscle were dissected as quickly as possible and homogenized in 7.5 volumes of homogenization buffer by a Polytron (Kinematic GmbH, Luzern, Switzerland) in the presence of a protease inhibitor cocktail to minimize protein degradation (see Ohlendieck et al., J. Cell Biol. 112: 135-148 (1991)). Homogenates were centrifuged for 15 min at 3,000 ×g and the supernatant filtered through 4 layers of cheese cloth. The pellets from this initial centrifugation step were rehomogenized and centrifuged as above and the supernatants of four repeated homogenization cycles combined. Membrane pellets were obtained by centrifugation of the combined supernatants for 35 min at 140,000×g and the final preparation was KCl-washed as described by Ohlendieck et al., *J. Cell Biol.* 112:135-148 (1991). Cardiac membranes from control and dystrophic dy/dy mice (C57BL/6J-dy; Jackson Laboratory, Bar Harbor, Me.) were prepared as described for control and mdx mouse muscle.

A newly established wheat germ agglutination procedure was employed to isolate purified skeletal muscle sarcolemma (see Ohlendieck et al. *J. Cell Biol.* 112:135-148 (1991)) and dystrophin-glycoprotein complex was prepared from rabbit skeletal muscle as described by Ervasti et al., (*Nature* 345:315-319 (1990)). Protein was determined as described by Peterson (*Anal. Biochem.* 83:346-356 (1977)) using bovine serum albumin as a standard.

Preparation of sheep antisera using native complex immunogen

Monospecific antibodies against the different components of the dystrophin-glycoprotein complex were produced by injecting the native dystrophin-glycoprotein complex purified as described herein into sheep. After testing the crude sheep antisera for the presence of antibodies against the dystrophin-glycoprotein complex, monospecific antibodies to 35 kDa glycoprotein, 43 kDa glycoprotein, 50 kDa glycoprotein and 59 kDa protein were affinity purified from individual Immobilon strips of the various components of the dystrophin-glycoprotein complex as described by Sharp et al., (*J. Biol. Chem.* 264:2816-2825 (1989)). Specificity of affinity-purified antibodies was subsequently determined by immunoblot analysis with rabbit sarcolemma and rabbit dystrophin-glycoprotein complex.

Monoclonal antibodies XIXCI to dystrophin, VIA4$_1$ to 50 kDa glycoprotein, McB2 to Na/K-ATPase (Urayama et al., *J. Biol. Chem.* 264:8271-8280 (1989)) and IID8 to cardiac $Ca^{2+}$-ATPase (Jorgensen et al., *Cell Motil Cytoskel.* 9:164-174 (1988)) were previously characterized by extensive immunofluorescence and immunoblot analysis (Ohlendieck et al., *J. Cell Biol.* 112:135-148 (1991)). Rabbit polyclonal antibodies against the C-terminal sequences of human dystrophin and human dystrophin-related protein (DRP) were affinity-purified and characterized as described (Ervasti et al., *J. Biol. Chem.* 266:9161-9165 (1991)). Monoclonal antibody SB-SP-1 against spectrin was purchased from Sigma Chemical Company (St. Louis, Mo.).

Gel electrophoresis and immunoblot analysis

Proteins were fractionated on 3-12% gradient SDS polyacrylamide gels and protein bands were visualized by Coomassie-blue staining and also analyzed by Stainsall staining. Proteins were transferred to nitrocellulose and immunoblot staining with antibodies and densitometric scanning was carried out as described above. Both protein A and protein G did not label primary sheep antibody sufficiently. Therefore, after primary labeling with sheep antibody, immunoblots of mouse muscle membranes were incubated with rabbit anti-sheep secondary antibody followed by incubation with $^{125}I$-labeled protein A (Amersham Corporation). This procedure gave reproducibly a very strong signal in autoradiography and enabled densitometric scanning of DAP antibody binding to control and mdx mouse muscle membranes.

Lectin-staining of immunoblots was carried out under optimized conditions as described (Campbell et al., *Nature* 338:259-262 (1989); Ohlendieck et al., *J. Cell Biol.* 112:135-148 (1991)). Blots were incubated for 1 hr with 1:1,000 diluted peroxidase-labeled wheat germ agglutinin, concanavalin A and jacalin (Vector Laboratories, Burlingame, Calif.) and developed in 20 mM Tris-Cl, pH 7.5, 200mM NaCl using 4-chloro-1-napthol as substrate (Jorgensen et al., *J. Cell Biol.* 110:1173-1185 (1990)).

Immunofluorescence microscopy

Immunofluorescence microscopy of 8 μm transverse cryosections from control, mdx and dy/dy mouse skeletal muscle was performed as described by Ohlendieck et al. (*J. Cell Biol.* 112: 135-148 (1991)). Following preincubation for 20 min with 5% normal goat antiserum in PBS (50 mM sodium phosphate, pH 7.4, 0.9% NaCl), cryosections were incubated for 1 hr at 37° C. with primary antibodies (1:1,000 dilution of crude antisera or 1:100 dilution of hybridoma supernatant or 1:50 dilution of affinity-purified antibodies). After extensive washing in PBS the sections were labeled with 1:100 diluted affinity-purified fluorescein-labeled goat anti-mouse IgG or goat anti-rabbit IgG (Boehringer-Mannheim) and subsequently examined in a Zeiss Axioplan fluorescence microscope. In the case of mouse monoclonal antibodies used on mouse cryosections, a biotin-streptavidin system was employed for immunodetection. Affinity-purified primary antibodies were biotinylated according to the instructions in the commercially available biotinylation kit from Amersham Corporation. Cryosections were incubated with biotinylated primary antibody as already described for unlabeled primary antibody and subsequently extensively washed in PBS. Finally, sections were fluorescently labeled by incubation with 1:100 diluted affinity-purified fluorescein-conjugated avidin (Sigma Chemical Company).

For labeling of skeleton muscle specimen with wheat germ agglutinin (WGA), cryosections were incubated with 1:2,000 diluted fluorescein-conjugated WGA (Sigma Chemical Company) for 30 min in the presence and absence of 0.3 M N-acetyl-glucosamine. Sections were intensively washed in PBS and then examined for specific labeling in a fluorescence microscope. Histochemical examination of control, mdx and dy/dy mouse skeletal muscle cryosections was performed by haematoxylin and eosin staining as described by Dubowitz (*Muscle Biopsy—A Practical Approach*, London:Bailliere Tindall, 1985, 2nd edition).

Immunofluorescence microscopy of biopsy specimens from patients afflicted with neuromuscular disorders was performed under identical conditions. Cryosections from healthy normal humans of varying age and sex and cryosections from patients suffering from a variety of different neuromuscular disorders (Duchenne muscular dystrophy, Bedker's muscular dystrophy, limb girdle dystrophy, congenital muscular dystrophy and spinal muscular atrophy) were placed on the same microscopy slide and the samples therefore treated in an identical manner during all incubation and washing steps, Human muscle biopsy specimen were obtained from the Departments of Pediatrics and Neuropathology, University of Iowa Clinics and Hospitals.

Immunoblot analysis of antibodies to dystrophin-associated proteins

Sheep antiserum raised against the native dystrophin-glycoprotein complex was used to affinity-purify monospecific antibodies to the individual components of the tightly associated dystrophin-glycoprotein complex. The high specificity of the eluted, affinity-purified antibodies was demonstrated by immunoblot. Sheep antibodies to 35 kDa glycoprotein, 43 kDa glycoprotein, 50 kDa glycoprotein and 59 kDa protein exhibited strong labeling of their respective antigen in sarcolemma and isolated dystrophin-glycoprotein complex from rabbit skeletal muscle. These results indicate monospecificity of the affinity-purified antibodies for the different components of the dystrophin-glycoprotein complex and this is a crucial prerequisite for the characterization of components of the complex in control, mdx and dy/dy muscle. Sheep antibodies to 156 kDa glycoprotein did not exhibit strong labeling in immunoblotting and furthermore the affinity-purification of sheep antibodies to 156 kDa glycoprotein is complicated due to contaminating fragments from degraded dystrophin molecules. We therefore used the already previously characterized monoclonal antibody VIA4$_1$ for the analysis of 156 kDa glycoprotein, which is a highly specific probe and exhibits strong labeling in immunoblotting.

Dystrophin-associated proteins in skeletal muscle membranes from mdx mouse

After characterization, the affinity-purified sheep antibodies were used in an extensive immunoblot analysis to compare the expression of components of the dystrophin-glycoprotein complex in skeletal muscle membranes from control and mdx mouse. Mdx mouse is a possible animal model from Duchenne muscular dystrophy which is missing dystrophin due a point mutation in the dystrophin gene. Skeletal muscle fibers from mdx mouse undergo cycles of degeneration and regeneration and it is therefore of considerable interest to examine the status of dystrophin-deficient mdx skeletal muscle. Coomassie-blue and "Stains-all" staining reveals that membrane preparations from control and mdx mouse skeletal muscle are similar in composition. Crude skeletal muscle membranes from mdx mouse are characterized by the absence of dystrophin but contain dystrophin-related protein in normal size and abundance as already previously described for purified sarcolemma.

Prior to the examination of the dystrophin-associated glycoproteins in mdx mouse muscle the general status of glycoproteins and sarcolemma components in the membrane preparation of mdx muscle used in this study was evaluated. It is important to account for possible secondary effects to proteins caused by the ongoing degeneration and regeneration cycles in mdx skeletal muscle fibers. Lectin-staining with wheat germ agglutinin-concanavalin A and jacalin showed that the glycoprotein composition with respect to these three lectins is very comparable in control and mdx mouse muscle membranes. Furthermore, plasma membrane marker Na/K-ATPase was found to be equally distributed in both membrane preparations. These results indicate that the general glycoprotein and sarcolemma protein composition is not severely affected in mdx mouse muscle.

Identical immunoblots were examined for the relative expression of dystrophin-associated proteins in skeletal muscle membranes from control and mdx mouse. The relative abundance of dystrophin-associated proteins of apparent 35 kDa, 43 kDa, 50 kDa, 59 kDa and 156 kDa proteins is greatly reduced in mdx muscle membranes. Densitometric scanning of $^{125}$I-protein A-labeled immunoblots, carried out as described above, revealed a 84%±3 reduction for 35 kDa glycoprotein, 80%±5% reduction for 43 kDa glycoprotein, 83%±5 reduction for 50 kDa glycoprotein, 86%±6 reduction for 59 kDa protein and approximately 80-90% reduction for 156 kDa glycoprotein in mdx muscle membranes when compared to control membranes. The comparative densitometric scanning was performed with individually isolated from five 10-week old control mice and five-week old mdx mice. A similarly reduced expression of dystrophin-associated proteins was also observed in membranes isolated from 5, 20 and 30-week old mdx mice as compared to age-matched control mice. The same results were obtained with crude skeletal muscle membranes, which had not been washed with 0.6 M KCl, and also with microsomal membranes prepared as described by Ohlendieck et al., *J. Cell. Biol.* 112:135–148 (1991). These findings indicate that mdx mouse skeletal muscle are not only deficient in dystrophin, but that in addition the density of the dystrophin-associated glycoproteins is greatly reduced in mdx mouse muscle.

Dystrophin-associated proteins in skeletal muscle membranes from dy/dy mouse Dystrophic skeletal muscle fibers from the animal model dy/dy mouse have a similar histochemical appearance to skeletal muscle fibers in human muscular dystrophy. However, the genetic locus for the neuromuscular disorder *dystrophia muscularis* was assigned to mouse chromosome 10. Muscle membranes from dy/dy mouse contain dystrophin of normal size and abundance making this animal model a very good control for the status of dystrophin-associated proteins in necrotic, but dystrophin-containing muscle tissue. Coomassie-blue staining revealed no apparent differences between membranes isolated from control and dy/dy mouse skeletal muscle and the density of dystrophin-related protein is also comparable between both membrane preparations. Most importantly, antibodies to the different dystrophin-associated proteins showed approximately equal amounts of these proteins in skeletal muscle membranes from control and dy/dy mouse. These findings demonstrate that dystrophin-associated proteins are not affected by secondary events in necrotic dy/dy muscle which contains dystrophin. Therefore, the reduced expression of dystrophin-associated proteins in skeletal muscle membranes from mdx mice is most likely a primary event following the absence of dystrophin from the membrane cytoskeleton of mdx muscle.

EXAMPLE 6

Distribution of Dystrophin-Associated Proteins in Normal and Dystrophic Human Tissue The results disclosed in Example 5 demonstrate the absence, or dramatic reduction in the abundance of, dystrophin-associated proteins in tissue samples from dystrophic mice. The present example discloses a similar finding in human tissue samples by immunofluorescence microscopy and immunoblot analysis.

Biopsy Specimens

Skeletal muscle biopsy specimens were obtained from original diagnostic specimens or discarded surgical material with the approval of the institutional review board for medical projects of the University of Iowa Hospitals and Clinics. Normal human skeletal muscle was obtained from the Department of Surgery, University of Iowa Hospitals and Clinics during routine surgical procedures involving different muscles from twenty individuals (6–70 years old) who had no clinical history of neuromuscular disorders. The analysis carried out in the present Example comprised skeletal muscle specimens from 12 DMD patients (3–14 years old) of the University of Iowa Hospitals and Clinics.

Cardiac DMD muscle was obtained at Texas Children's Hospital, Baylor College of Medicine from a 12 year old boy. For comparative purposes, a large number of muscle samples from patients afflicted with other neuromuscular disorders were investigated. These samples were obtained from patients seen in the Adult and Pediatric Neuromuscular Clinics at the University of Iowa Hospitals and Clinics. Besides the routine histopathological diagnosis, muscle biopsy specimens from patients afflicted with neuromuscular disorders were tested for dystrophin. Patient biopsy specimens were quick-frozen in liquid nitrogen-cooled isopentane and stored frozen at $-80°$ C. until use.

Immunofluorescence Microscopy

Immunofluorescence microscopy of 7 $\mu$m cryosections from human skeletal muscle specimens was performed as previously described for rabbit muscle. Antibodies used in the experiments described in this Example were from various sources. Monoclonal antibody (mAb) IVD$3_1$ to 50-DAG, mAb IIH6 to 156-DAG, mAbs VIA$4_2$ and XIXC2 to dystrophin were produced and characterized as described previously. The antibodies to dystrophin do not immunologically cross-react with spectrin, $\alpha$-actin or dystrophin-related protein and furthermore stain exclusively the sarcolemma of normal human and mouse muscle cryosections, but not DMD or mdx mouse muscle cells, which are lacking dystrophin. Therefore the antibodies used in this investigation are specific probes for human dystrophin which is an important prerequisite for the diagnosis of Duchenne muscular dystrophy and related neuromuscular disorders. Highly specific antibodies against the dystrophin-glycoprotein complex were raised in sheep using the purified dystrophin-glycoprotein complex. Antibodies to the individual components of the dystrophin-glycoprotein complex were affinity-purified from individual Immobilon-P transfer membrane strips as described. While satisfactory immunoblot and immunofluorescence staining of muscle membranes and cryosections from normal and mdx mice was obtained with the serum taken after the first booster injection (see Example 5), human muscle membranes and cryosections were labeled much more strongly by sheep serum taken after a further booster injection with purified dystrophin-glycoprotein complex. Rabbit antibodies to the last 12 amino acids of the C-terminus of dystrophin-related protein (DRP) were previously characterized and do not immunologically cross-react with dystrophin. Monoclonal antibody SB-SP-1 to spectrin was purchased from Sigma Chemical Company.

Depending on the secondary antibodies used, cryosections of skeletal muscle were pre-incubated for 20 min with 5% normal goat serum in PBS (50 mM sodium phosphate, pH 7.4, 0.9% NaCl) or 5% normal rabbit serum in PBS supplemented with 5% bovine serum albumin. Subsequently cryosections were treated in a 1-h incubation at 37° C. with different dilutions of primary antibody. After washing in PBS sections were labeled at 37° C. with 1:200 diluted affinity-purified fluorescein-labeled goat anti-mouse IgG (Boehringer-Mannheim) and subsequently examined in a Zeiss Axioplan fluorescence microscope. In the case of primary sheep antibodies, cryosections were washed in PBS and then incubated for 30 min at 37° C. with 1:500 diluted biotinylated rabbit anti-sheep IgG (Vector Laboratories). Finally, after washing in PBS cryosections were labeled for 30 min at 37° C. with 1:1000 diluted fluorescein-conjugated avidin (Sigma Chemical Company). For labeling of skeletal muscle specimens with wheat germ agglutinin (WGA) cryosections were incubated with 1:1,000 diluted fluorescein-conjugated WGA (Sigma Chemical Company) for 30 min in the presence and absence of 0.3 M N-acetyl-glucosamine.

Prior to the characterization of dystrophin-associated proteins in DMD patients, all human skeletal muscle cryosections used in this investigation were characterized by labeling with antibodies to dystrophin and spectrin, as well as stained with wheat germ agglutinin. In contrast to dystrophin, which is completely missing in DMD skeletal muscle, it was found that the membrane cytoskeletal protein spectrin labels evenly the cell periphery of skeletal muscle fibers from DMD patients. Because this investigation evaluates the status of sarcolemmal glycoproteins the overall wheat germ agglutinin (WGA) staining of different muscle specimens was also examined. Both normal human and DMD skeletal muscle exhibited strong WGA-labeling of the cell periphery, which could be specifically eliminated by pre-incubation with the competitive sugar N-acetylglucosamine. In addition to muscle cell surface staining, normal and especially DMD skeletal muscle showed strong lectin binding to the endomysial and perimysial connective tissue. These findings indicate that the majority of WGA-binding components of the skeletal muscle cell periphery are not affected in DMD. This is important in analyzing of the status of dystrophin-associated glycoproteins in DMD muscle. In addition, it was previously shown that no general depletion of plasma membrane glycoproteins occurs in DMD skeletal muscle.

Sheep antibodies to the individual components of the dystrophin-glycoprotein complex, the specificity of which was previously characterized in normal and mdx mouse muscle, were used to evaluate the status of dystrophin-associated proteins in muscle biopsy specimens from DMD patients. Immunofluorescence staining revealed restricted labeling of dystrophin-associated proteins to the cell periphery of normal human muscle fibers. Skeletal muscle cryosections exhibited no staining of the interior of myofibers suggesting a specific association of dystrophin-associated proteins with the sarcolemma membrane of human skeletal muscle. This was previously established for mouse and rabbit skeletal muscle using subcellular fractionation studies and immunofluorescence microscopy. In order to reliably compare all muscle biopsy specimens, cryosections were all placed on the same microscopy slide, labeled with the same concentration of primary and secondary antibodies and were treated in an identical way during all incubation and washing steps. Undiluted affinity-purified sheep antibodies in combination with a biotin-streptavidin system were used for immunodetection. Photographs were taken under identical conditions with the same exposure time so that a direct comparison of immunofluorescence staining intensity could be undertaken. The immunofluorescence analysis of the DMD skeletal muscle specimen reveals the general loss of dystrophin-associated glycoproteins in all 12 DMD patients investigated. Histological examination of DMD skeletal muscle, stained with hematoxylin and eosin, showed severe dystrophic degeneration with a rounded contour of muscle cells, central nucleation, a marked variability of fiber size diameter, scattered necrotic muscle fibers and increased interstitial fibrosis typical for DMD muscle. While the cell periphery of DMD skeletal muscle specimens exhibits normal amounts of spectrin, strong staining for WGA in interstitial connective tissue and a complete lack of dystrophin, it exhibits a drastic loss of 156-DAG, 59-DAP, 50-DAG, 43-DAG and 35-DAG. This was observed in all DMD muscle fibers and did not correlate with the severity of degeneration of individual skeletal muscle fibers. However it should be noted that immunofluorescence staining is not only reduced, but the muscle cell periphery is discontinuously labeled in a patchy fashion. In stark contrast to DMD, dystrophin-associated proteins exhibited normal- immunofluorescence labeling of the skeletal muscle cell periphery from patients suffering from limb girdle dystrophy, congenital muscular dystrophy and spinal muscular atrophy. These results demonstrate that a deficiency in dystrophin in human DMD skeletal muscle is accompanied by a specific and substantial reduction in all of the dystrophin-associated proteins.

The results obtained with affinity-purified sheep antibodies to 50-DAG were confirmed by immunofluorescence microscopy with monoclonal antibody IVD3$_1$ against 50-DAG. A 1:100 dilution of IVD3$_1$ hybridoma supernatant produced satisfactory results. Biopsy specimens from DMD patients of varying ages exhibited very low levels of immunofluorescence staining intensity for 50-DAG when directly compared to normal age-matched human muscle. Similar to the results obtained with affinity-purified sheep antibodies, immunofluorescence staining with mAb IVD3$_1$ varied in the degree of reduction between individual DMD cases. Besides drastic reduction of immunofluorescence staining intensity, labeling of 50-DAG was observed to be discontinuous in the skeletal muscle cell periphery of DMD patients.

To investigate the status of 50-DAG in necrotic muscle fibers which show no deficiency in dystrophin, specimens from a variety of other neuromuscular disorders were labeled with mAb IVD3$_1$. 50-DAG was found in normal amounts in the cell periphery of muscles from patients afflicted with limb girdle dystrophy, congenital muscular dystrophy and spinal muscular atrophy. Biopsy specimens from two patients suffering from facioscapulohumeral muscular dystrophy and a patient afflicted with Friedreich's ataxia also exhibited normal immunofluorescence labeling of the muscle cell periphery for 50-DAG. These are important findings because they suggest that dystrophin-associated glycoproteins are not severely affected by secondary effects in muscle fiber degeneration. The loss of dystrophin-associated proteins appears to be directly related to a deficiency in the cytoskeletal component dystrophin and was observed in all DMD skeletal muscle fibers independent of the severity of muscle degeneration.

Immunoblot analysis of total human muscle membranes

In order to quantitate the remaining amounts of dystrophin-associated proteins in DMD skeletal and cardiac muscle membranes, immunoblot analysis of total muscle membranes was carried out. Total SDS muscle extracts are routinely used to evaluate the status of the high molecular weight component dystrophin and 156 kDa dystrophin-associated protein in patients. In contrast, total SDS-extracts are not suitable for the study of low molecular weight proteins due to the high density of low molecular weight muscle proteins. Therefore a total membrane fraction of skeletal and cardiac muscle was used to investigate the low molecular weight components of the dystrophin-glycoprotein complex. In addition, an obvious difficulty in studying dystrophin-associated glycoproteins in DMD muscle membranes was the very restricted amount of muscle tissue obtainable from diagnostic biopsies. This problem was overcome by acquiring 2-5 grams of DMD skeletal muscle during spinal fusion surgery. After arrival in the laboratory the tissue was washed in ice-cold phosphate-buffered saline and then immediately processed for centrifugation. The starting material for preparations of cardiac membranes was approximately 1 g of human heart samples. Control cardiac muscle included explanted heart tissue from a transplant patient and a cardiac autopsy specimen from another individual obtained shortly after death. Muscle samples were homogenized and centrifuged in 7.5 volumes of 20 mM sodium pyrophosphate, 20 mM sodium phosphate monohydrate, 1 mM MgCl2, 0.303 M sucrose, 0.5 mM EDTA, pH 7.0 at 1,100$\times$g as described in Example 5. All buffers used were supplemented with a protease inhibitor cocktail to prevent protein degradation. To obtain total membranes, supernatants were filtered through cheese cloth and centrifuged at 135,000$\times$g for 37 min. Samples were stored in small aliquots at $-135°$ C. until use. Protein concentration was determined using bovine serum albumin as standard. Membrane proteins were fractionated on 3-12% gradient SDS polyacrylamide gels and transferred to nitrocellulose membranes. Immunoblot staining with antibodies and densitometric scanning of radioactively labeled immunoblots was performed as described previously.

DMD skeletal muscle membranes exhibited increased amounts of dystrophin-related protein but lacked dystrophin. Staining with peroxidase-conjugated lectins (wheat germ agglutinin, concanavalin A, jacalin) did not show differences in the major glycoprotein composition of both membrane preparations. Coomassie-blue staining revealed a comparable overall protein composition of normal and DMD skeletal muscle membranes. However, all of the dystrophin-associated proteins were found to be reduced in DMD skeletal muscle membranes when compared to a membrane preparation from age-matched normal human muscle. Densitometric scanning of identical immunoblots which were labeled with $^{125}$I-labeled Protein-A revealed an approximately 90% reduction for all of the dystrophin-associated proteins in DMD skeletal muscle membranes. The reduction of dystrophin-associated proteins in muscle membranes from DMD patients observed in immunoblotting confirms the finding of a lower density of all of the dystrophin-associated proteins in DMD skeletal muscle cryosections. The fact that dystrophin-associated proteins are detectable in the DMD muscle cell periphery by immunofluorescence microscopy and in DMD muscle membranes by immunoblotting suggests that remaining dystrophin-associated proteins are not present in the cytoplasm but are localized to the sarcolemma membrane and are not degraded.

After establishing the reduction of dystrophin-associated proteins in cryosections and total membranes from DMD skeletal muscle, the status of the individual components of the dystrophin-glycoprotein complex in cardiac DMD muscle was also investigated. Antibodies to dystrophin-associated proteins did not exhibit satisfactory immunofluorescence labeling of human cardiac muscle thus we were not able to investigate their status in cardiac DMD cryosections.

Total membranes from normal human and DMD cardiac specimens were separated by 3–12% SDS-PAGE and analyzed by immunoblotting. Normal human cardiac muscle contains all of the components of the dystrophin-glycoprotein complex as previously found for rabbit skeletal muscle. Cardiac DMD muscle membranes, which completely lacked dystrophin, exhibited near to normal amounts of dystrophin-related protein. By contrast all of the dystrophin-associated proteins were greatly reduced and this is analogous to the findings in skeletal muscle membranes from DMD patients. Densitometric scanning of $^{125}$I-labeled Protein-A immunoblots showed approximately 90% reduction for all of the dystrophin-associated proteins in human cardiac DMD muscle. Immunoblot analysis of two patients afflicted with inherited cardiomyopathy showed similar amounts of all of the components of the dystrophin-glycoprotein complex when directly compared to normal human cardiac muscle. In summary, immunoblotting of total muscle membranes enabled the quantitation of the remaining amounts of the individual components of the dystrophin-glycoprotein complex in skeletal and cardiac DMD muscle. The immunoblot data agrees with the results from immunofluorescence microscopy that all of the dystrophin-associated proteins are dramatically reduced in DMD muscle.

EXAMPLE 7

Primary Structure of the 43 kDa and 156 kDa Dystrophin-Associated Proteins

The primary sequence of two dystrophin-associated proteins has been established by cDNA cloning and DNA sequencing. In this Example, it is shown that the transmembrane 43 kDa and extracellular 156 kDa dystrophin-associated glycoproteins are encoded by a single mRNA and that the extracellular 156 kDa DAG binds laminin.

Cloning and primary sequence analysis of a precursor protein for the 43/156 kDa DAG Affinity purified guinea pig polyclonal antibodies to the 43 kDa DAG were prepared as described by Ervasti and Campbell, Cell 66:1121–1131 (1991)) and used to screen $2 \times 10^6$ clones of λgt11 expression library. Clone R43-A with a length of 600 base pairs was isolated from a random primed adult rabbit skeletal muscle λgt11 library by immunoscreening. An oligo-dT primed rabbit skeletal muscle cDNA library in λ zapII (Stratagene) was screened at high stringency with a $^{32}$P-labelled cDNA insert from the R43-A clone (random primed labelling kit, Boehringer Mannheim Biochemicals). Clone R43-B overlaps R43-A and extends ~1 kb in the 5' direction. Further clones were isolated from λgt11 libraries: R43-D - random primed λgt11 library, R43-C - oligo-dT primed λgt11 library. To isolate cDNA extending to the 5'-end of mRNA (clone R43-E), a rabbit skeletal muscle cDNA library was constructed using random primed cDNA with λgt11 vector (Stratagene). All cDNA inserts were sequenced either on an Applied Biosystems Incorporated Automatic Sequencer or manually by the dideoxy chain termination method. Sequences were analyzed with the Genetics Computer Group Inc. (Wisconsin package) and PCGene (Intelligenetics) Software.

The 4200 nucleotide cDNA shown in the SEQ ID NO: 1 sequence contains a 2685 nucleotide open reading frame (beginning at nucleotide 170) coding for a polypeptide od 895 amino acids with a calculated molecular mass of 97,029. The first 29 amino acids of the open reading frame are predominantly hydrophobic and likely represent a signal peptide. Hydropathy analysis identified a single continuous region of 24 amino acids close to the C-terminal showing characteristics of a transmembrane domain. Four potential N-linked glycosylation sites and numerous potential phosphorylation sites are found in the 97 kDa polypeptide. Finally, no significant sequence homology was detected in the NBRF database between any known proteins and the predicted amino acid sequence of the 97 kDa polypeptide.

Biochemical characterization of the dystrophin-glycoprotein complex has demonstrated that the 43 kDa DAG has hydrophobic properties characteristic of a transmembrane protein and contains Asn-linked oligosaccharides. These properties are consistent with the predicted sequence of the C-terminal half of the 97 kDa polypeptide which contains a potential transmembrane domain and three out of four potential sites for N-glycosylation. The C-terminal origin of 43 kDa DAG was confirmed using an antibody raised in a rabbit against a synthetic peptide corresponding to the 15 C-terminal amino acid residues of the deduced sequence. This anti-peptide antibody specifically recognized the 43 kDa DAG. In addition, peptide sequence determined directly from the 43 kDa DAG matched 783–793 residues of the deduced amino acid sequence of the 97 kDa polypeptide.

N-terminal domain of the 97 kDa precursor encodes 156 kDa DAG

In order to identify the N-terminal domain of the 97 kDa precursor polypeptide, antibodies to different regions of the 97 kDa precursor polypeptide were produced by expressing several overlapping cDNAs encoding different regions in the 97 kDa precursor polypeptide. A set of pGEX vectors (Smith and Johnson, Gene 67:31–40, (1988)) were used to express various fragments of DNA for 97 kDa precursor protein as E. coli fusion proteins. Fusion protein-A (FP-A) contains residues 665–856 corresponding to the cDNA R43-A found in the expression library with affinity-purified antiserum against 43 kDa DAG. Fusion protein-C (FP-C) contains residues 857–895 which are the C-terminal 38 amino acids of the 97 kDa precursor polypeptide, and does not overlap with FP-A. Fusion protein-B (FP-B) contains residues 367–863 and thus overlaps with FP-A and FP-C, and has a portion of the N-terminal region of the 97 kD precursor, which is not present in the mature 43 kDa DAG. Fusion protein-D (FP-D) contains residues 62–438 and thus contains only the N-terminal region of the 97 kDa precursor polypeptide. The correct construction of the recombinant plasmids was verified by restriction mapping. To construct FP-A, the EcoRI insert from R43-A clone with the size of 0.6 kb was cloned into the EcoRI site of pGEX-1. FP-B was constructed by ligation EcoRI insert from R43-B clone (1.5 kb) into the EcoRI site of pGEX-2T. FP-C was made by ligation into the BamHI site of pGEX-1 the BamHI fragment of cDNA R43-C, containing C-terminal sequence with stop codon, representing last 38 amino acids. For the FP-D construct, EcoRI insert (1.2 kb) from R43-D was inserted into pGEX-2T vector digested with EcoRI. Each recombinant molecule was introduced in *E. coli* DH5a cells. Overnight cultures were diluted 1:10, incubated for one hour and induced for 2 hours with 1 mM IPTG. Cells were resuspended in PBS and sonicated. Fusion proteins were purified from supernatant by affinity chromatography on glutathione-Sepharose (Pharmacia) and eluted with 5 mM glutathione. Dystrophin-glycoprotein complex was isolated as described Lesot et al. (*Cell* 66:1121–1131 (1991)). Sheep polyclonal antibodies to the purified DGC were produced as described Ohlendieck and Campbell (*J. Cell Biol.* 115:1685–1694 (1991)) and antifusion protein antibodies were affinity purified from polyclonal antiserum. A peptide representing the 15 carboxyl-terminus amino acids of the 97 kDa cDNA (PKNMTPYRSPPPYVP) was obtained from the HHMI Peptide Facility (Washington University, St. Louis) as the N-terminal p-benzoylbenzoyl-peptide photoprobe. Peptide was conjugated to keyhole limpet hemocyanin, mixed with Freund's complete adjuvant and injected into a rabbit as immunogen. SDS-PAGE was carried out on 3–12% gradient gels in the presence of 1% 2-mercaptoethanol and transferred to nitrocellulose for immunoblot analysis.

Affinity-purified antibodies were then tested using each fusion protein and purified DGC. Consistent with the C-terminal domain encoding the 43 kDa DAG, antibodies to FP-A and FP-C specifically stained both bands of 43 kDa DAG doublet. However, antibodies to FP-B stained the 43 kDa DAG and the 156 kDa DAG components of DGC. Thus, a second product of 97 kDa precursor polypeptide appears to be the 156 kDa DAG. In accordance with this supposition, antibodies to FP-D stain only 156 kDa DAG. Therefore, posttranslational processing of 97 kDa precursor polypeptide gives rise to two components of DGC: 43 kDa DAG and 156 kDa DAG. Biochemical studies have demonstrated that 156 kDa DAG is not an integral membrane protein and contains N-linked and O-linked glycosylation. These properties are consistent with the predicted N-terminal half of the 97 kDa precursor which does not possess any hydrophobic region, has one potential N-linked glycosylation site and many potential O-glycosylation sites.

Expression of 43/156 kDa DAG in muscle and non-muscle tissues

Tissue distribution of 43/156 kDa DAG was examined by Northeastern blot analysis. Total RNA was isolated by homogenization in RNAzol (Cinna/Biotecx, TX) followed by chloroform extraction. Poly(A) RNA was enriched by oligo-dT cellulose chromatography and resolved on 1.2% agarose gels containing 5% formaldehyde. RNA was transferred to Genescreen Nylon Membranes (NEN Research Products, MA). Prehybridization was performed at 42° C. in 5×SSC, 5×Denhardt's solution, 50% formamide, 10% dextran sulfate and 100 μg/ml of salmon sperm DNA. Probes were hybridized overnight at 42° C. at a specific activity of at least 1×10$^6$ cpm/ml. Membranes were washed at 62° C. in 2×SSC, 0.1% SDS and were exposed to film (X-OMAT AR, Kodak) at −80° C.

A prominent 5.8 kb transcript was detected in mRNA from rabbit skeletal muscle, cardiac muscle and lung. A weaker hybridizing transcript of the same size was found in brain. Northern blot analysis with total RNA from variety of tissues: liver, kidney, diaphragm and stomach also detected a 5.8 kb mRNA in all these tissues. Thus, the 5.8 kb transcript for the 43/156 kDa DAG is present in various muscle and non-muscle tissues, most likely originating from the same gene.

Identification of the 43/156 kDa DAG in muscle and non-muscle tissues was performed using immunoblots of membranes from different tissues and affinity-purified antibodies to FP-B (43/156 kDa specific). Total membranes were prepared from tissues homogenized in 7.5 volumes of homogenization buffer (20 mM sodium pyrophosphate, 20 mM sodium phosphate monohydrate, 1 mM MgCl$_2$, 0.3 M sucrose, 0.5 mM EDTA, pH 7.0) using a Polytron PTS-10-S probe (Kinematic GmbH, Luzern, Switzerland) in the presence of a protease inhibitor cocktail. Homogenates were centrifuged for 15 min at 1100×g and the supernatant filtered through cheese cloth. The supernatants of four repeated homogenizations were combined and centrifuged for 35 min at 140,000×g. The final membrane preparations were KCl-washed as previously described. Immunoblot analysis was performed as previously using 250 μg of skeletal muscle membranes and 500 μg of non-muscle membranes.

The 43 kDa DAG was detected in isolated membranes from skeletal muscle, brain, cardiac muscle and lung. The 156 kDa DAG was detected in skeletal and cardiac muscle membranes, but was slightly lower in molecular weight in cardiac membranes. In brain and lung membranes the molecular weight of the "156 kDa" DAG reactive protein was ∼120 kDa. The variability in molecular weight for the "156 kDa" reactive protein is maybe due to differential glycosylation of the core protein in muscle versus non-muscle tissues.

mRNA and protein expression in dystrophic muscle

RNA blot analysis of skeletal muscle mRNA from control and mdx mice of different ages using cDNA probe R43-B to 43/156 kDa mRNA revealed no reduction of 43/156 kDa DAG mRNA in mdx mice vs control mice. However, as previously observed, the 43 kDa DAG is greatly reduced in mdx skeletal muscle membranes. Thus, the absence of dystrophin causes no change in the mRNA for the 43/156 kDa DAG but leads to dramatic reductions in the amount of the 43 kDa DAG and 156 kDa DAG in skeletal muscle. Analysis of mRNA from control and DMD skeletal muscle also showed no difference in 43/156 kDa DAG mRNA expression. In agreement with findings in mdx mouse muscle, indirect immunofluorescence analysis of cryosections from normal and DMD skeletal muscle with 156 kDa specific (anti FP-D) and 43 kDa specific (anti FP-A) antibodies demonstrated a drastically reduced density of 43 kDa DAG and 156 kDa DAG in skeletal muscle of a DMD patient. Thus, 43/156 kDa DAG encoding gene is transcribed and specific mRNA is still present at the normal level in dystrophic muscle, but the 43 kDa DAG and 156 kDa DAG are greatly reduced in dystrophic muscle.

Since the 43/156 kDa DAG is expressed in non-muscle tissues we also examined expression of 43 kDa DAG in non-muscle tissues of control and mdx mice. The 156 kDa DAG could not be tested because polyclonal antibodies to the protein core of rabbit 156 kDa DAG described above do not cross react with the 156 DAG in mouse muscle. Immunoblot analysis of brain and kidney membranes from control and mdx mice, stained with polyclonal anti FP-A antibodies (43 kDa specific), revealed no reduction in the amount of 43 kDa DAG in these mdx tissues. Thus, the dramatic reduction of the 43 kDa DAG that is found in mdx mice appears to be restricted to skeletal muscle and is not found in non-muscle tissues.

156 kDa DAG binds laminin

To test for the association of the 156 DAG with the extracellular matrix, rabbit skeletal muscle surface membranes and pure DGC were electrophoretically separated, transferred to the nitrocellulose membranes and overlaid with $^{125}$I-labeled laminin. More specifically, rabbit skeletal muscle crude membranes, sarcolemma membranes and dystrophin-glycoprotein complex were electrophoretically separated on 3–12 % SDS polyacrylamide gels in the presence of 1% 2-mercaptoethanol and transferred to nitrocellulose. Purified laminin mouse EHS (Sigma) was iodinated With $^{125}$I Na using a lactoperoxdase/glucose oxidase reaction by the Diabetes, Endocrinology Research Center at the University of Iowa. The [$^{125}$I]-laminin overlay procedure of Smalheiser and Schwartz (*Proc. Natl. Acad. Sci. USA* 84, 6457–6461, (1987)) was performed as described except that nitrocellulose transfers were blocked with 5 % nonfat dry milk in 150 mM NaCl, 50 mM sodium phosphate, pH 7.5. To test for co-immunoprecipitation of laminin and the 156 Ka dystrophin-associated glycoprotein, pH 12 extracts (Ervasti et al., *Nature* 345, 315–319 (1990)) of rabbit skeletal muscle surface membranes were incubated for 24 h at 4° C. with gentle mixing buffer A (0.14 M NaCl, 1 mM CaCl$_2$, mMMgCl$_2$, 10mM triethanolasine-HCl, pH 7.6) in the absence or presence of 50 μg of purified mouse EHS laminin (Sigma), then incubated for an additional 24 h at 4° C. with 100 ml of either protein A-Sepharose or anti-laminin/ protein A-Sepharose which had been equilibrated with 3% BSA in buffer A and washed four times with buffer A. The Sepharose was pelleted by a brief centrifugation, the supernatant (void) decanted and the Sepharose washed three times with buffer A. Equivalent volumes of the resulting voids and washed Sepharose pellets were analyzed by SDS-polyacrylamide gel electrophoresis and immunoblotting using monoclonal antibody IIH6 which is specific for the 156 kDa DAG.

A single laminin binding band, corresponding to the 156 kDa DAG Was detected in surface membranes and purified DGC. Binding of $^{125}$I-laminin to the 156 kDa DAG was significantly decreased by a 1000-fold excess of unlabeled laminin demonstrating the specificity of $^{125}$I-laminin binding to the 156 kDa DAG. $^{125}$I-Fibronectin did not label the 156 kDa DAG or any other component of the DGC, nor did a 1000-fold excess of nonradioactive fibronectin have any effect on the binding of $^{125}$I-laminin to the 156 kDa DAG. The interaction of 156 kDa DAG with laminin was also shown by co-immunoprecipitation of laminin and 156 kDa DAG. Anti-laminin antibodies did not precipitate the 156 kDa DAG from alkaline extracts of rabbit skeletal muscle surface membranes. This result was consistent with the observation that the surface membranes used were devoid of laminin, merosin, or S-laminin as detected on immunoblots using specific antibodies. However, anti-laminin antibodies effectively precipitated the 156 kDa DAG from alkaline extracts which had been preincubated with exogenously added laminin. These results suggest that the 156 kDa DAG specifically binds laminin and may mediate interaction of DGC to extracellular matrix.

EXAMPLE 8

Human cDNA Clone

The rabbit specific insert clone R43-B (corresponding to the 156/43 coding region) was used to probe a human skeletal muscle library in λgt10. Screening of 106 clones was performed with a $^{32}$P-labeled cDNA insert from R43-B rabbit clone (random primed labeling kit, Boehringer Mannheim). Hybridization was performed in 2×Pipes, 50% deionized formamide, 0.5% SDS, 100 μg/ml denatured salmon sperm DNA with 106 counts/ml of probe at 42° C. overnight. Washes were done in 0.1×SSC, 0.1% SDS at 65° C. The first human clone isolated was designated HD-1 (~2.6kb) Clones HD-2 (~3.3kb) and HD-3 (~4.1 kb) were isolated from the same human library using 5′ KpnI fragment from the HD-1 clone under similar hybridization conditions.

The chromosomal linkage of the 156 kDa and 43 kDa glycoproteins was determined by analysis of a panel of human/hamster cell hybrids (Bios, Corp.). Using a isotopically labeled cDNA insert from clone R43-B, hybridization with human genomic DNA and hamster DNA was performed. This experiment enabled the distinction between the human and hamster genes. The same probe was then used to analyze DNA from 25 human/hamster cell hybrids which showed that the 156/43 kDa sequence was linked to human chromosome 3.

EXAMPLE 9

Dystrophin-Associated Protein in Autosomal Muscular Dystrophy Affected Tissue Autosomal muscular dystrophy is a form of muscular dystrophy resulting from a mutation which maps to an autosome. It has been determined that in most cases of autosomal muscular dystrophy, dystrophin is present in affected tissue at near normal levels. This example discloses, however, that in muscle tissue from an individual afflicted with autosomal muscular dystrophy, levels of all of the dystrophin-associated proteins are substantially reduced.

Muscle biopsy tissue from an individual afflicted with autosomal Fukuyama congenital muscular dystrophy (FCMD) was prepared in sections as described, for instance, in Examples 4 and 5. The tissue samples were contacted with affinity purified sheep primary antibodies followed by fluorescein labeled secondary antibodies as described previously. Tissue samples from normal human muscle and Duchenne muscle were similarly treated as control samples.

Dystrophin and all of the dystrophin-associated glycoproteins were found to be present in normal tissue, but absent or substantially reduced in DMD muscle. However, in FCMD tissue immunostaining for all of the dystrophin-associated glycoproteins was diminished while dystrophin was not substantially reduced.

EXAMPLE 10

Reduction in Level of 50 kDa Dystrophin-Associated Protein in Severe Childhood Autosomal Recessive Muscular Dystrophy In a first experiment, the pattern of expression of dystrophin and dystrophin-associated proteins in biopsied skeletal muscle was analyzed by immunohistochemical techniques. Skeletal muscle biopsy samples were obtained from a 5-year old male with SCARMD, a 10-year old male with SCARMD, an 11-year old female with SCARMD and an 11-year old male with SCARMD. The diagnosis of SCARMD was made based on the following: 1) DMD-like phenotype affecting both males and females, 2) mode of inheritance compatible with an autosomal recessive disease, 3) North African patients, 4) elevated serum creatine kinase level and 5) normal expression of dystrophin in biopsied skeletal muscle analyzed by both immunohistochemistry and immunoblotting (Khurana et al., Neuromusc. Dis. 1: 185-194 (1991)). Control samples included a biopsy sample from a 16-year old male with no pathological changes in skeletal muscle and an 8-year old male with DMD.

Serial transverse cryosections were immunostained with VIA4$_2$, a monoclonal antibody against dystrophin, and affinity-purified sheep polyclonal antibodies against 156 kDa, 59 kDa, 50 kDa, 43 kDa and 35 kDa dystrophin-associated proteins as described above.

In normal skeletal muscle, antibodies against dystrophin and dystrophin-associated proteins stained the sarcolemma. In related experiments, no abnormality of these proteins was observed in biopsy samples from individuals afflicted with the following neuromuscular diseases: limb-girdle muscular dystrophy, myotonic dystrophy, facioscapulohumeral muscular dystrophy, oculopharyngeal muscular dystrophy, non-Fukuyama type congenital muscular dystrophy, congenital fiber type disproportion, spinal muscular atrophy and amyotrophic lateral sclerosis. In DMD patients, dystrophin was absent and the immunostaining for all of the dystrophin-associated proteins was substantially reduced in the sacrolemma, except at the neuromuscular junction and in the sarcolemma of intrafusal muscle fibers.

However, in all four SCARMD patients including two siblings, immunostaining for the 50 kDa dystrophin-associated protein was substantially reduced in the sarcolemma of all muscle fibers including the neuromuscular junction and the sarcolemma of intrafusal muscle fibers, while immunostaining for dystrophin, 156 kDa, 59 kDa and 43 kDa was preserved. The loss of 50 kDa dystrophin-associated protein in SCARMD patients was more severe than in DMD patients. Immunostaining for 35 kDa dystrophin-associated protein in SCARMD patients was reduced compared with normal control but was not so severely reduced as in DMD patients.

Loss of the 50 kDa dystrophin-associated protein in the sarcolemma of SCARMD patients was confirmed using three other specific antibodies against the 50 kDa dystrophin-associated protein. These antibodies included a IVD3$_1$ (a monoclonal antibody against the 50 kDa dystrophin-associated protein), a sheep polyclonal antibody affinity-purified against the 50 kDa dystrophin-associated protein peptide disclosed in SEQ ID NO:2 and an affinity-purified guinea pig polyclonal antibody.

In a second experiment, designed to confirm the deficiency of the 50 kDa dystrophin-associated protein in SCARMD patients, immunoblot analysis of skeletal muscle biopsy SDS extracts was performed. Biopsy samples were obtained from a 5-year old male with SCARMD, a 41-year old female with facioscapulohumeral muscular dystrophy, a 10-year old male with n-o pathological changes in the skeletal muscle and an 11-year old female with SCARMD. Cryosections from skeletal muscle biopsy specimens were homogenized in 50 volumes of SDS-extraction buffer (80 mM Tris HCl (pH 6.8), 10% SDS, 0.115 M sucrose, 1% β-mercaptoethanol, 1 mM PMSF, 1 mM benzamidine and 1 mM EDTA) and incubated at 50° C. for 10 minutes. After centrifugation, 10 μl of samples were separated on a 3-12% polyacrylamide gel. The gel was stained with Coomassie blue and the density of the myosin heavy chain (MHC) band was measured using a computing laser densitometer (Model 300S; Molecular Dynamics, Sunnyvale, Calif.). Based on this result, samples were run on a 3-12% polyacrylamide gel so that the amount of MHC was equal for all specimens. Transfer to the nitrocellulose membrane and immunostaining with antibodies were performed as described above.

The antibodies used in the staining procedure included polyclonal antibodies against the last 10 amino acids of dystrophin (ANTI-DYS), a monoclonal antibody against the 156 kDa dystrophin-associated protein (IIH6) and a mixture of affinity-purified sheep polyclonal antibodies against the 59 kDa, 50 kDa and 43 kDa dystrophin-associated proteins. The affinity purified sheep polyclonal antibody against the 35 kDa dystrophin-associated protein was not strong enough to stain the 35 kDa dystrophin-associated protein in crude muscle extracts.

While dystrophin, 156 kDa dystrophin-associated protein, 59 kDa dystrophin-associated protein and 43 kDa dystrophin-associated protein were detected, 50 kDa dystrophin-associated-protein was undetectable in all four SCARMD patients.

EXAMPLE 10

Determination of 50 kDa Dystrophin-Associated Protein Antioenic Peptide Sequence The components of the purified dystrophin glycoprotein complex were separated by polyacrylamide gel electrophoresis followed by transfer to nitrocellulose paper to form a protein transfer blot. The 50 kDa species was separated from other components of the protein transfer blot, and subjected to trypsin digestion using standard protocols. Digestion products were separated by reverse phase HPLC and subjected to protein sequence analysis. Five peptide sequences were determined through this set of experiments. These sequences are provided as SEQ ID NOS:2-6.

One peptide sequence, Pro Arg Pro Leu Ser Thr Leu Pro Met Phe (SEQ ID NO:2) was chemically synthesized and attached to a solid support to generate an affinity matrix. An affinity column was prepared using this matrix and a polyclonal antibody preparation, prepared by immunizing animals with purified dystrophin-glycoprotein complex, was passed over the column. Polyclonal antibodies specifically reactive with this peptide were isolated using this affinity purification method. Thus, the peptide sequence identified represents an immunogenic epitope of the 50 kDa dystrophin-associated protein.

Peptides identified in this manner can be used to immunize animals to generate antibodies specifically reactive with a single epitope of the 50 kDa protein. In addition, degenerate probes can be designed which can then be used in combination with conventional molecular biological techniques to isolate the gene which encodes the 50 kDa dystrophin-associated protein.

Equivalents

Those skilled in the art will recognize or be able to ascertain, using no more than routine experimentation, many equivalents to the specific embodiments of the invention described herein. Such equivalents are intended to be encompassed by the claims which follow the sequence listing.

---

We claim:

1. A method for aiding in the diagnosis of severe childhood autosomal recessive muscular dystrophy comprising:
   a) providing an experimental mammalian muscle tissue sample, treated if necessary to render components of the dystrophin-glycoprotein complex available for antibody binding;
   b) contacting the experimental mammalian muscle tissue sample from step a) with a first antibody which specifically binds to the 50 kDa dystrophin-associated protein, and a second antibody which specifically binds to a component of the dystrophin-glycoprotein complex selected from the group consisting of dystrophin and dystrophin-associated proteins having molecular weights of about 25 kDa, 35 kDa, 43 kDa, 59 kDa and 156 kDa, under conditions appropriate for antibody binding;
   c) detecting and characterizing the extent of binding of the antibodies to the experimental mammalian muscle tissue sample; and
   d) comparing the extent of binding of the antibodies to the experimental mammalian muscle tissue sample, to the extent of binding determined for a normal mammalian muscle tissue sample treated as in steps a)-c), a substantial reduction in the extent of binding to the 50 kDa dystrophin-associated protein, in combination with detectable binding to the component of the dystrophin-glycoprotein complex selected from the group consisting of dystrophin and dystrophin-associated proteins having molecular weights of about 25 kDa, 35 kDa, 43 kDa, 59 kDa and 156 kDa, being indicative of severe childhood autosomal recessive muscular dystrophy.

2. A method of claim 1 wherein the experimental muscle tissue sample is a skeletal muscle tissue sample.

3. A method for aiding in the diagnosis of severe childhood autosomal recessive muscular dystrophy, comprising:
   a) providing experimental mammalian muscle tissue samples prepared for immunohistochemical analysis;
   b) contacting a first experimental mammalian muscle tissue sample with a first antibody which specifically binds to the 50 kDa dystrophin-associated protein;
   c) contacting a second experimental mammalian muscle tissue sample with a second antibody which specifically binds to a component of the dystrophin-glycoprotein complex selected from the group consisting of (i) dystrophin and (ii) dystrophin associated proteins having molecular weights of about 156 kDa, 59 kDa, and 43 kDa;

d) detecting and characterizing the extent of binding of the first antibody and the second antibody to the neuromuscular junction region and the non-neuromuscular junction region of the muscle cells in the first and the second experimental mammalian skeletal muscle tissue sample, respectively; and e) comparing the extent of specific binding of the first antibody and the second antibody to the first and the second experimental mammalian muscle tissue sample, respectively, to the extent of specific binding determined for a normal mammalian muscle tissue sample treated as in steps a)–d), a substantial reduction in the extent of antibody binding to the 50 kDa dystrophin-associated protein in both neuromuscular junction and non-neuromuscular junction regions of the mammalian muscle tissue sample together with preservation of antibody binding to a component of the dystrophin-glycoprotein complex selected from the group consisting of (i) dystrophin and (ii) dystrophin-associated proteins having molecular weights of about 25 kDa, 59 kDa, and 43 kDa being indicative of severe childhood autosomal recessive muscular dystrophy.

4. A method of claim 3 wherein the experimental muscle tissue sample is a skeletal muscle tissue sample.

5. A method for aiding in the diagnosis of severe childhood autosomal recessive muscular dystrophy, comprising:

a) providing a protein transfer blot from an experimental mammalian muscle tissue sample;

b) contacting the protein transfer blot from the experimental mammalian muscle tissue sample from step a) with a first antibody which specifically binds to the 50 kDa dystrophin-associated protein, and a second antibody which specifically binds to a component of the dystrophin-glycoprotein complex selected from the group consisting of dystrophin and dystrophin-associated proteins having molecular weights of about 25 kDa, 35 kDa, 43 kDa, 59 kDa and 156 kDa, under conditions appropriate for antibody binding;

c) detecting and characterizing the extent of binding of the antibodies to the protein transfer blot from the experimental mammalian muscle tissue sample; and d) comparing the extent of binding of the antibodies to the protein transfer blot from the experimental mammalian muscle tissue sample, to the extent of binding determined for a protein transfer blot from a normal mammalian muscle tissue sample treated as in steps a)–c), a substantial reduction in the extent of binding to the 50 kDa dystrophin-associated protein, in combination with detectable binding to the component of the dystrophin-glycoprotein complex selected from the group consisting of dystrophin and dystrophin-associated proteins having molecular weights of about 25 kDa, 35 kDa, 43 kDa, 59 kDa and 156 kDa, being indicative of severe childhood autosomal recessive muscular dystrophy.

6. A method of claim 5 wherein the experimental muscle tissue sample is a skeletal muscle tissue sample.

7. A substantially pure antibody preparation produced by affinity purification using the amino acid sequence of SEQ ID NO: 2, which antibody is characterized by the ability to specifically bind to the 50 kDa component of the dystrophin-glycoprotein complex present in serial transverse cryosections of mammalian skeletal muscle.

* * * * *

SEQUENCE LISTING (1) GENERAL INFORMATION:

(iii) NUMBER OF SEQUENCES: 6

(2) INFORMATION FOR SEQ ID NO:1:

(i) SEQUENCE CHARACTERISTICS:
        (A) LENGTH: 4200 base pairs
        (B) TYPE: nucleic acid
        (C) STRANDEDNESS: double
        (D) TOPOLOGY: linear (ii) MOLECULE TYPE: cDNA (ix) FEATURE:
        (A) NAME/KEY: CDS
        (B) LOCATION: 170..2855

(xi) SEQUENCE DESCRIPTION: SEQ ID NO:1:

```
GGCTGCTTTT CAGGAAGATA AAGCTTTTAA GGCTGCCTAA CACTAGAAGG AGAGGCTCTC          60

GATGCTCTGG GATGGAGCAG GTGTGCAGAG GGTGAGGACC CGGCTCTGGG ATCAAGTCAC         120

TTGCTTGCTT CCTTAGCAAG ATCTTCGGCT TGAGCGAACT TGGCCTGGG ATG AGG            175
                                                       Met Arg
                                                        1

ATG TCT GTG GGC CTT TCA CTG CTG CTC CCC TTG TGG GGG AGG ACA TTT          223
Met Ser Val Gly Leu Ser Leu Leu Leu Pro Leu Trp Gly Arg Thr Phe
          5              10                  15

CTC CTC CTC CTC TGT GTG GCC GTG GCT CAG TCC CAT TGG CCC AGC GAA          271
Leu Leu Leu Leu Cys Val Ala Val Ala Gln Ser His Trp Pro Ser Glu
     20                  25                  30

CCC TCG GAG GCT GTC AGG GAC TGG GAG AAC CAG CTG GAG GCG TCC ATG          319
Pro Ser Glu Ala Val Arg Asp Trp Glu Asn Gln Leu Glu Ala Ser Met
 35                  40                  45                  50

CAC TCT GTG CTC TCA GAC CTG CAC GAA GCC CTT CCC ACA GTG GTT GGC          367
His Ser Val Leu Ser Asp Leu His Glu Ala Leu Pro Thr Val Val Gly
                 55                  60                  65

ATT CCT GAT GGC ACG GCT GTT GTT GGG CGC TCG TTT CGA GTG ACC ATT          415
Ile Pro Asp Gly Thr Ala Val Val Gly Arg Ser Phe Arg Val Thr Ile
             70                  75                  80

CCA ACA GAT TTA ATT GGC TCC AGT GGA GAA GTC ATC AAG GTA TCC ACG          463
Pro Thr Asp Leu Ile Gly Ser Ser Gly Glu Val Ile Lys Val Ser Thr
         85                  90                  95

GCA GGG AAG GAG GTT TTG CCA TCG TGG CTG CAT TGG GAT CCA CAG AGC          511
Ala Gly Lys Glu Val Leu Pro Ser Trp Leu His Trp Asp Pro Gln Ser
    100                 105                 110

CAC ACC CTG GAG GGC CTT CCG CTG GAC ACG GAC AAG GGT GTG CAT TAC          559
His Thr Leu Glu Gly Leu Pro Leu Asp Thr Asp Lys Gly Val His Tyr
115                 120                 125                 130

ATC TCA GTG AGC GCT GCA CAG CTG GAT GCC AAC GGA AGC CAC ATC CCT          607
Ile Ser Val Ser Ala Ala Gln Leu Asp Ala Asn Gly Ser His Ile Pro
                135                 140                 145

CAG ACC TCC AGT GTG TTC TCC ATC GAG GTC TAC CCC GAA GAC CAC AGT          655
Gln Thr Ser Ser Val Phe Ser Ile Glu Val Tyr Pro Glu Asp His Ser
            150                 155                 160
```

| | | | | | | | | | | | | | | | | |
|---|---|---|---|---|---|---|---|---|---|---|---|---|---|---|---|---|
| GAG | CCG | CAG | TCT | GTG | CGG | GCG | GCC | TCT | CCA | GAC | CTG | GGC | GAG | GCG | GCG | 703 |
| Glu | Pro | Gln | Ser | Val | Arg | Ala | Ala | Ser | Pro | Asp | Leu | Gly | Glu | Ala | Ala | |
| | | 165 | | | | 170 | | | | | 175 | | | | | |
| GCG | TCT | GCC | TGT | GCT | GCC | GAG | GAG | CCG | GTG | ACC | GTC | TTG | ACC | GTG | ATT | 751 |
| Ala | Ser | Ala | Cys | Ala | Ala | Glu | Glu | Pro | Val | Thr | Val | Leu | Thr | Val | Ile | |
| | 180 | | | | | 185 | | | | | 190 | | | | | |
| CTG | GAT | GCC | GAT | CTC | ACC | AAG | ATG | ACT | CCG | AAG | CAG | AGG | ATC | GAC | CTC | 799 |
| Leu | Asp | Ala | Asp | Leu | Thr | Lys | Met | Thr | Pro | Lys | Gln | Arg | Ile | Asp | Leu | |
| 195 | | | | | 200 | | | | | 205 | | | | | 210 | |
| CTG | CAC | AGG | ATG | CAG | AGC | TTC | TCG | GAG | GTG | GAG | CTC | CAC | AAC | ATG | AAG | 847 |
| Leu | His | Arg | Met | Gln | Ser | Phe | Ser | Glu | Val | Glu | Leu | His | Asn | Met | Lys | |
| | | | | 215 | | | | | 220 | | | | | 225 | | |
| TTG | GTG | CCG | GTG | GTG | AAT | AAC | AGA | CTG | TTT | GAT | ATG | TCT | GCC | TTC | ATG | 895 |
| Leu | Val | Pro | Val | Val | Asn | Asn | Arg | Leu | Phe | Asp | Met | Ser | Ala | Phe | Met | |
| | | | 230 | | | | | 235 | | | | | 240 | | | |
| GCC | GGC | CCC | GGA | AAC | GCC | AAA | AAG | GTG | GTA | GAG | AAC | GGG | GCC | CTG | CTC | 943 |
| Ala | Gly | Pro | Gly | Asn | Ala | Lys | Lys | Val | Val | Glu | Asn | Gly | Ala | Leu | Leu | |
| | | | 245 | | | | | 250 | | | | | 255 | | | |
| TCC | TGG | AAG | CTG | GGC | TGC | TCC | CTG | AAC | CAG | AAC | AGT | GTG | CCT | GAC | ATT | 991 |
| Ser | Trp | Lys | Leu | Gly | Cys | Ser | Leu | Asn | Gln | Asn | Ser | Val | Pro | Asp | Ile | |
| | 260 | | | | | 265 | | | | | 270 | | | | | |
| CGC | GGC | GTG | GAG | GCC | CCT | GCC | AGG | GAG | GGC | ACT | ATG | TCT | GCC | CAG | CTT | 1039 |
| Arg | Gly | Val | Glu | Ala | Pro | Ala | Arg | Glu | Gly | Thr | Met | Ser | Ala | Gln | Leu | |
| 275 | | | | | 280 | | | | | 285 | | | | | 290 | |
| GGC | TAC | CCT | GTG | GTG | GGT | TGG | CAC | ATT | GCC | AAC | AAG | AAG | CCA | CCT | CTC | 1087 |
| Gly | Tyr | Pro | Val | Val | Gly | Trp | His | Ile | Ala | Asn | Lys | Lys | Pro | Pro | Leu | |
| | | | | 295 | | | | | 300 | | | | | 305 | | |
| CCC | AAG | CGT | ATC | CGA | AGG | CAG | ATC | CAT | GCC | ACA | CCC | ACA | CCT | GTC | ACT | 1135 |
| Pro | Lys | Arg | Ile | Arg | Arg | Gln | Ile | His | Ala | Thr | Pro | Thr | Pro | Val | Thr | |
| | | | 310 | | | | | 315 | | | | | 320 | | | |
| GCC | ATT | GGG | CCC | CCA | ACC | ACG | GCC | ATC | CAG | GAG | CCG | CCG | TCC | AGG | ATC | 1183 |
| Ala | Ile | Gly | Pro | Pro | Thr | Thr | Ala | Ile | Gln | Glu | Pro | Pro | Ser | Arg | Ile | |
| | | 325 | | | | | 330 | | | | | 335 | | | | |
| GTG | CCT | ACC | CCC | ACT | TCT | CCA | GCC | ATT | GCT | CCT | CCC | ACA | GAG | ACG | ATG | 1231 |
| Val | Pro | Thr | Pro | Thr | Ser | Pro | Ala | Ile | Ala | Pro | Pro | Thr | Glu | Thr | Met | |
| | | 340 | | | | | 345 | | | | | 350 | | | | |
| GCT | CCT | CCA | GTC | AGG | GAT | CCT | GTT | CCT | GGG | AAG | CCC | ACG | GTC | ACC | ACT | 1279 |
| Ala | Pro | Pro | Val | Arg | Asp | Pro | Val | Pro | Gly | Lys | Pro | Thr | Val | Thr | Thr | |
| 355 | | | | | 360 | | | | | 365 | | | | | 370 | |
| CGG | ACT | CGA | GGT | GCC | ATT | ATT | CAG | ACC | CCA | ACC | CTA | GGC | CCC | ATC | CAG | 1327 |
| Arg | Thr | Arg | Gly | Ala | Ile | Ile | Gln | Thr | Pro | Thr | Leu | Gly | Pro | Ile | Gln | |
| | | | | 375 | | | | | 380 | | | | | 385 | | |
| CCC | ACT | CGG | GTG | TCA | GAC | GCT | GGC | ACC | GTA | GTT | TCT | GGC | CAG | ATT | CGT | 1375 |
| Pro | Thr | Arg | Val | Ser | Asp | Ala | Gly | Thr | Val | Val | Ser | Gly | Gln | Ile | Arg | |
| | | | 390 | | | | | 395 | | | | | 400 | | | |
| GCA | ACG | GTG | ACC | ATT | CCT | GGC | TAC | GTG | GAG | CCC | ACA | GCA | GTT | GCC | ACC | 1423 |
| Ala | Thr | Val | Thr | Ile | Pro | Gly | Tyr | Val | Glu | Pro | Thr | Ala | Val | Ala | Thr | |
| | | 405 | | | | | 410 | | | | | 415 | | | | |
| CCT | CCC | ACA | ACT | AC. | ACC | AAA | AAG | CCA | CGA | GTG | TCC | ACA | CCA | AAA | CCA | 1471 |
| Pro | Pro | Thr | Thr | Thr | Thr | Lys | Lys | Pro | Arg | Val | Ser | Thr | Pro | Lys | Pro | |
| | | 420 | | | | | 425 | | | | | 430 | | | | |
| GCA | ACG | CCT | TCA | ACG | GAC | TCC | TCA | GCC | ACC | ACG | ACT | CGC | AGG | CCA | ACC | 1519 |
| Ala | Thr | Pro | Ser | Thr | Asp | Ser | Ser | Ala | Thr | Thr | Thr | Arg | Arg | Pro | Thr | |
| 435 | | | | | 440 | | | | | 445 | | | | | 450 | |
| AAG | AAG | CCA | CGG | ACA | CCC | AGG | CCG | GTG | CCA | CGG | GTC | ACC | ACT | AAA | GCT | 1567 |
| Lys | Lys | Pro | Arg | Thr | Pro | Arg | Pro | Val | Pro | Arg | Val | Thr | Thr | Lys | Ala | |
| | | | | 455 | | | | | 460 | | | | | 465 | | |
| CCC | ATC | ACC | AGG | CTG | GAG | ACG | GCC | TCC | CCA | CCT | ACT | CGT | ATC | CGC | ACC | 1615 |
| Pro | Ile | Thr | Arg | Leu | Glu | Thr | Ala | Ser | Pro | Pro | Thr | Arg | Ile | Arg | Thr | |
| | | | | 470 | | | | | 475 | | | | | 480 | | |
| ACC | ACC | AGC | GGG | GTG | CCC | CGC | GGG | GGA | GAA | CCC | AAC | CAG | CGC | CCA | GAG | 1663 |

|  |  |  |  |  |  |  |  |  |  |  |  |  |  |  |  |  |
|---|---|---|---|---|---|---|---|---|---|---|---|---|---|---|---|---|
| Thr | Thr | Ser<br>485 | Gly | Val | Pro | Arg<br>490 | Gly | Gly | Glu | Pro | Asn | Gln<br>495 | Arg | Pro | Glu | |
| CTC | AAG | AAC | CAC | ATC | GAC | AGG | GTG | GAC | GCC | TGG | GTC | GGC | ACC | TAC | TTT | 1711 |
| Leu | Lys<br>500 | Asn | His | Ile | Asp | Arg<br>505 | Val | Asp | Ala | Trp | Val<br>510 | Gly | Thr | Tyr | Phe | |
| GAG | GTG | AAG | ATC | CCA | TCT | GAT | ACC | TTC | TAC | GAC | AAG | GAG | GAT | ACC | ACC | 1759 |
| Glu<br>515 | Val | Lys | Ile | Pro<br>520 | Ser | Asp | Thr | Phe | Tyr<br>525 | Asp | Lys | Glu | Asp | Thr<br>530 | Thr | |
| ACC | GAC | AAG | CTC | AAG | CTG | ACC | CTG | AAG | CTG | CGA | GAG | CAG | CAG | CTG | GTG | 1807 |
| Thr | Asp | Lys | Leu | Lys<br>535 | Leu | Thr | Leu | Lys | Leu<br>540 | Arg | Glu | Gln | Gln | Leu<br>545 | Val | |
| GGC | GAG | AAG | TCC | TGG | GTG | CAG | TTC | AAC | AGC | AAC | AGC | CAG | CTC | ATG | TAT | 1855 |
| Gly | Glu | Lys | Ser<br>550 | Trp | Val | Gln | Phe | Asn<br>555 | Ser | Asn | Ser | Gln | Leu<br>560 | Met | Tyr | |
| GGC | CTG | CCC | GAC | AGC | AGC | CAC | GTG | GGC | AAA | CAC | GAG | TAT | TTC | ATG | CAT | 1903 |
| Gly | Leu | Pro<br>565 | Asp | Ser | Ser | His | Val<br>570 | Gly | Lys | His | Glu | Tyr<br>575 | Phe | Met | His | |
| GCC | ACA | GAC | AAG | GGA | GGC | CTG | TCC | GCC | GTG | GAT | GCC | TTT | GAG | ATC | CAT | 1951 |
| Ala | Thr<br>580 | Asp | Lys | Gly | Gly | Leu<br>585 | Ser | Ala | Val | Asp | Ala<br>590 | Phe | Glu | Ile | His | |
| GTC | CAC | AAG | CGC | CCT | CAA | GGG | GAC | AAA | GCT | CCT | GCT | CGT | TTC | AAA | GCC | 1999 |
| Val<br>595 | His | Lys | Arg | Pro | Gln<br>600 | Gly | Asp | Lys | Ala | Pro<br>605 | Ala | Arg | Phe | Lys | Ala<br>610 | |
| AAG | TTC | GTG | GGT | GAC | CCA | GCG | CCA | GTG | GTG | AAT | GAC | ATC | CAC | AAG | AAG | 2047 |
| Lys | Phe | Val | Gly | Asp<br>615 | Pro | Ala | Pro | Val | Val<br>620 | Asn | Asp | Ile | His | Lys<br>625 | Lys | |
| ATT | GCC | CTG | GTG | AAG | AAG | CTG | GCC | TTT | GCC | TTT | GGG | GAT | CGC | AAT | TGC | 2095 |
| Ile | Ala | Leu | Val<br>630 | Lys | Lys | Leu | Ala | Phe<br>635 | Ala | Phe | Gly | Asp | Arg<br>640 | Asn | Cys | |
| AGC | ACC | GTC | ACC | CTG | CAG | AAC | ATC | ACC | CGC | GGC | TCC | ATT | GTG | GTG | GAG | 2143 |
| Ser | Thr | Val<br>645 | Thr | Leu | Gln | Asn | Ile<br>650 | Thr | Arg | Gly | Ser | Ile<br>655 | Val | Val | Glu | |
| TGG | ACC | AAC | AAC | ACA | CTG | CCG | CTG | GAG | CCC | TGC | CCC | AAG | GAG | CAG | ATC | 2191 |
| Trp | Thr<br>660 | Asn | Asn | Thr | Leu | Pro<br>665 | Leu | Glu | Pro | Cys | Pro<br>670 | Lys | Glu | Gln | Ile | |
| ACG | GGG | CTG | AGC | CGC | AGG | ATC | GCC | GAG | GAC | AAC | GGG | CAG | CCT | CGG | CCA | 2239 |
| Thr | Gly | Leu<br>675 | Ser | Arg | Arg | Ile | Ala<br>680 | Glu | Asp | Asn | Gly | Gln<br>685 | Pro | Arg | Pro<br>690 | |
| GCC | TTC | ACC | AAT | GCC | CTG | GAG | CCT | GAC | TTT | AAG | GCC | ACG | AGC | ATC | GCC | 2287 |
| Ala | Phe | Thr | Asn | Ala<br>695 | Leu | Glu | Pro | Asp | Phe<br>700 | Lys | Ala | Thr | Ser | Ile<br>705 | Ala | |
| ATA | ACG | GGC | TCT | GGC | AGT | TGT | CGG | CAC | TTG | CAG | TTT | ATC | CCC | GTG | GCA | 2335 |
| Ile | Thr | Gly | Ser<br>710 | Gly | Ser | Cys | Arg | His<br>715 | Leu | Gln | Phe | Ile | Pro<br>720 | Val | Ala | |
| CCG | CCT | GGG | ATC | CCG | TCC | TCG | GTG | ACA | CCA | CCC | ACG | GAG | GTG | CCA | GAC | 2383 |
| Pro | Pro | Gly<br>725 | Ile | Pro | Ser | Ser | Val<br>730 | Thr | Pro | Pro | Thr | Glu<br>735 | Val | Pro | Asp | |
| AGG | GAC | CCC | GAG | AAG | AGC | AGT | GAG | GAT | GAC | GTC | TAC | CTA | CAC | ACA | GTC | 2431 |
| Arg | Asp<br>740 | Pro | Glu | Lys | Ser | Ser<br>745 | Glu | Asp | Asp | Val | Tyr<br>750 | Leu | His | Thr | Val | |
| ATT | CCG | GCT | GTG | GTG | GTG | GCG | GCC | ATC | CTG | CTC | ATT | GCT | GGC | ATC | ATT | 2479 |
| Ile<br>755 | Pro | Ala | Val | Val | Val<br>760 | Ala | Ala | Ile | Leu | Leu<br>765 | Ile | Ala | Gly | Ile | Ile<br>770 | |
| GCC | ATG | ATC | TGC | TAC | CGC | AAG | AAG | CGG | AAG | GGC | AAG | CTC | ACC | CTG | GAG | 2527 |
| Ala | Met | Ile | Cys | Tyr<br>775 | Arg | Lys | Lys | Arg | Lys<br>780 | Gly | Lys | Leu | Thr | Leu<br>785 | Glu | |
| GAC | CAG | GCC | ACC | TTC | ATC | AAG | AAG | GGG | GTG | CCC | ATC | ATC | TTT | GCA | GAC | 2575 |
| Asp | Gln | Ala | Thr<br>790 | Phe | Ile | Lys | Lys | Gly<br>795 | Val | Pro | Ile | Ile | Phe<br>800 | Ala | Asp | |
| GAG | CTG | GAC | GAC | TCC | AAG | CCC | CGG | CCC | TCC | TCC | AGC | ATG | CCG | CTG | ATC | 2623 |
| Glu | Leu<br>805 | Asp | Asp | Ser | Lys | Pro<br>810 | Pro | Pro | Ser | Ser | Ser<br>815 | Met | Pro | Leu | Ile | |

-continued

| | | | | | | | | | | | | | | | | |
|---|---|---|---|---|---|---|---|---|---|---|---|---|---|---|---|---|
| CTG | CAG | GAG | GAG | AAG | GCT | CCC | CTT | CCC | CCC | CCA | GAG | TAT | CCC | AGC | CAG | 2671 |
| Leu | Gln | Glu | Glu | Lys | Ala | Pro | Leu | Pro | Pro | Pro | Glu | Tyr | Pro | Ser | Gln | |
| | 820 | | | | 825 | | | | | 830 | | | | | | |
| AGC | GTG | CCC | GAG | ACC | ACG | CCT | CTG | AAC | CAG | GAC | ACT | GTG | GGG | GAG | TAC | 2719 |
| Ser | Val | Pro | Glu | Thr | Thr | Pro | Leu | Asn | Gln | Asp | Thr | Val | Gly | Glu | Tyr | |
| 835 | | | | | 840 | | | | 845 | | | | | 850 | | |
| ACG | CCC | CTT | CGG | GAT | GAG | GAT | CCC | AAC | GCG | CCT | CCC | TAC | CAG | CCC | CCC | 2767 |
| Thr | Pro | Leu | Arg | Asp | Glu | Asp | Pro | Asn | Ala | Pro | Pro | Tyr | Gln | Pro | Pro | |
| | | | | 855 | | | | | 860 | | | | | 865 | | |
| CCA | CCC | TTC | ACA | GCC | CCG | ATG | GAG | GGC | AAG | GGC | TCC | CGT | CCC | AAG | AAC | 2815 |
| Pro | Pro | Phe | Thr | Ala | Pro | Met | Glu | Gly | Lys | Gly | Ser | Arg | Pro | Lys | Asn | |
| | | | 870 | | | | | 875 | | | | | 880 | | | |
| ATG | ACC | CCT | TAC | CGG | TCA | CCC | CCT | CCT | TAT | GTT | CCC | CCT | T AACCCACAAG | | | 2865 |
| Met | Thr | Pro | Tyr | Arg | Ser | Pro | Pro | Pro | Tyr | Val | Pro | Pro | | | | |
| | | 885 | | | | | 890 | | | | | 895 | | | | |

CGCCTGGGTG GAGGCAGGGT AGGGCAGGGG CCTGGGGACA ACACAGTGTT GTCTGTGGAG 2925
CCCGGTGGCC CGCAGACCAT CGCCCACTGG GCGCTGACAC CAGACCTAGC ACACACTGGC 2985
ACACGGGGCC TGGACAAGCC CGCCCTCTCT GGTCCTCCCA AACCCCAAAG CAGCTGGAGA 3045
GACTTTGGGG ACTTTTTTTA TTTTTATTTT TTGCCTAACA GCTTTTTGTT TGTTCATAGA 3105
AAATCCTTCG CTGCGTTTTG ATGGCTGGCT CTGGAAGCAC CATTTGGAGT AGAGGTAGAG 3165
GGAGGGAGCG AGGAGCCGTG GGTGAACTCG CAGGCAGTGC TGGGCAGCCC CCCGGCTCTC 3225
TGCGTTTTGC CTTTAACACT AACTGTACTG TTTTTTCTAT TCACGTGTGT CTAGCTGCAG 3285
GATGTAACAT GGAAAACAGT AGCTAAAGAT TAAATTCAAA GGACTTTCAG AAGTTAAGGT 3345
TAAGTTTTTA CATTTAATCT GCTGTTTACC TAAACTTGTA TGTATAATTT TTGGGTGGGT 3405
ATGGGGAATT GCTTGCTAAA AATAAGCTC CCAGGGTGTT TCAAACTTAA GAGAAGACCA 3465
AGGGACAGTA TTTTTTATCA AAGGAATCCT ATTTTTTCAC ACTATGTCAA CTTGGTTGCT 3525
CTGATATCCC AGAGCCCGAT CGGGGGCCTC CTGGCCCTGG CTCAGGGGCC AGGGTCCTGG 3585
TGCTGGGTTT GCTCTCCTGC TGTTGGCAGG AGTTGGAAGC TGGAGGGGCC TCTCGGGCCG 3645
TGGACATCCC CACCTCCACC CCATGCATGC TAGTGGCCCA CCACCAAGGG GTCTTCATTT 3705
CCATGGGAAA GGGACTCCAA GAGGCAGTGG TGGCCGTGGC CCCCACCCCG GGTGCTCCAA 3765
GGTGGGCCAG CTGCTCGTGG GGGCCCCTGG GGAGGTTGAG GGACTCGACC ACATCGACCT 3825
GTTTCCTTTC ACCTTTTATT TTTTTTTTTC CCCACCCCTC CTAAAAGGAT TATCACGGTT 3885
TTTGAAACAC TCAGTGGGGG ACATTTTGGT GAAGATGCAA TATTTTTATG TCATGTGATG 3945
CTCTTTCCTC ACTTGACCTT GGCCACTTTG TCCCAACAGT CCACAGCCCC GCCCCGATCC 4005
ACCCCATCCC TCTTCTCTGG CGCTCCCGTC CCAGGCCTTG GGCCTGAACG ACTGGAAAAG 4065
GCCTGGTTGG CTGGGGAGGA GTGCCACCAA TAGTTCATAG TAAACAATCT GTGGGCTCTC 4125
AAAGCTAATT TTTTACTAAA GTTTTTATAC AGCCTCAAAT TGTTTTATTA AAAAATAGAT 4185
TAAAAATGGT GATGC 4200

( 2 ) INFORMATION FOR SEQ ID NO:2:

( i ) SEQUENCE CHARACTERISTICS:
        ( A ) LENGTH: 10
        ( B ) TYPE: amino acid ( i i ) MOLECULE TYPE: Peptide ( x i ) SEQUENCE DESCRIPTION: SEQ ID NO:2:

Pro Arg Pro Leu Ser Thr Leu Pro Met Phe            10

( 2 ) INFORMATION FOR SEQ ID NO:3:

( i ) SEQUENCE CHARACTERISTICS:
    ( A ) LENGTH: 9
    ( B ) TYPE: amino acid ( i i ) MOLECULE TYPE: Peptide ( x i ) SEQUENCE DESCRIPTION: SEQ ID NO:3:

His Asp Val Glu Glu Val Leu Pro Pro ( 2 ) INFORMATION FOR SEQ ID NO:4:

( i ) SEQUENCE CHARACTERISTICS:
    ( A ) LENGTH: 14
    ( B ) TYPE: amino acid ( i i ) MOLECULE TYPE: Peptide ( x i ) SEQUENCE DESCRIPTION: SEQ ID NO:4:

Glu Val Pro Arg Pro Leu Ser Thr Leu Pro Met Phe Asn Val ( 2 ) INFORMATION FOR SEQ ID NO:5:

( i ) SEQUENCE CHARACTERISTICS:
    ( A ) LENGTH: 7
    ( B ) TYPE: amino acid ( i i ) MOLECULE TYPE: Peptide ( x i ) SEQUENCE DESCRIPTION: SEQ ID NO:5:

Phe Val His Thr Leu Glu Pro ( 2 ) INFORMATION FOR SEQ ID NO:6:

( i ) SEQUENCE CHARACTERISTICS:
    ( A ) LENGTH: 9
    ( B ) TYPE: amino acid ( i i ) MOLECULE TYPE: Peptide ( x i ) SEQUENCE DESCRIPTION: SEQ ID NO:6:

Leu Ala Thr Ser Xaa Ile Gln Met Val